US011911067B2

(12) United States Patent
Townsend et al.

(10) Patent No.: US 11,911,067 B2
(45) Date of Patent: Feb. 27, 2024

(54) CIRCUMCISION APPARATUSES AND METHODS

(71) Applicant: ZatCo LLC, Fishers, IN (US)

(72) Inventors: Jackson Alexander Townsend, Zionsville, IN (US); Matthew Raymond Zielinski, Fishers, IN (US); Reuben Quincey Zielinski, Fishers, IN (US); Robert Anderson Till, Avon, IN (US)

(73) Assignee: ZATCO LLC, Fishers, IN (US)

( * ) Notice: Subject to any disclaimer, the term of this patent is extended or adjusted under 35 U.S.C. 154(b) by 0 days.

(21) Appl. No.: 17/457,889

(22) Filed: Dec. 6, 2021

(65) Prior Publication Data

US 2022/0087704 A1 Mar. 24, 2022

Related U.S. Application Data

(60) Provisional application No. 62/121,932, filed on Dec. 6, 2020.

(51) Int. Cl.
*A61B 17/326* (2006.01)
*A61B 17/32* (2006.01)

(52) U.S. Cl.
CPC .............. *A61B 17/326* (2013.01); *A61B 2017/320064* (2013.01)

(58) Field of Classification Search
CPC .............. A61B 17/326; A61B 2017/320064
USPC ........................................... 606/118
See application file for complete search history.

(56) References Cited

U.S. PATENT DOCUMENTS

| | | | |
|---|---|---|---|
| 2,376,893 A * | 5/1945 | Baker | A61B 17/326 606/118 |
| 4,491,136 A | 1/1985 | LeVeen | |
| 5,439,466 A | 8/1995 | Kilejian | |
| 5,797,921 A | 8/1998 | Cimini et al. | |
| 5,860,988 A | 1/1999 | Rawlings | |
| 6,660,012 B2 | 12/2003 | Lahiji | |
| 8,080,018 B2 | 12/2011 | Kostrzewski | |
| 8,142,444 B2 | 3/2012 | Mansour | |
| 8,597,304 B2 | 12/2013 | Kostrzewski | |
| 8,647,348 B2 | 2/2014 | Chiu et al. | |
| 8,777,962 B1 | 7/2014 | Poplin et al. | |
| 8,974,471 B2 | 3/2015 | Fuerst et al. | |
| 8,979,869 B2 | 3/2015 | Starr | |

(Continued)

*Primary Examiner* — Wade Miles
*Assistant Examiner* — Bridget E. Rabaglia

(57) ABSTRACT

A circumcision device and methods for using and manufacturing the same are disclosed. Embodiments of the circumcision device include a connector that permits the circumcision device to be connected by hand to and disconnected by hand from a tissue holding member while the tissue holding member is holding penile tissue. The connector permits the circumcision device to rotate while connected to the tissue holding member. Embodiments include a blade (cutting member) that is bent at an angle that may be oblique, and the blade may include a slot on either side of or across the bend. Further embodiments include at least one gripping member that extends perpendicularly to the axis the device rotates around, while additional embodiments include at least one gripping member that is aligned with the connector to assist in connection and removal of the device from a tissue holding member.

20 Claims, 34 Drawing Sheets

(56) References Cited

U.S. PATENT DOCUMENTS

| | | |
|---|---|---|
| 9,204,894 B2 | 12/2015 | Jianzhong |
| 9,289,217 B2 | 3/2016 | Fuerst et al. |
| 9,345,512 B2 | 5/2016 | Altokhais |
| 9,445,835 B2 | 9/2016 | Melhem et al. |
| 9,539,023 B2 | 1/2017 | Marotte |
| 9,539,024 B2 | 1/2017 | Shang et al. |
| 10,076,355 B2 | 9/2018 | Mohiuddin et al. |
| 10,179,006 B2 | 1/2019 | Zhao |
| 10,398,468 B2 | 9/2019 | Van Wyk |
| 10,702,301 B2 | 7/2020 | Liu |
| 10,952,766 B2 | 3/2021 | Parker et al. |

\* cited by examiner

CIRCUMCISION APPARATUSES AND METHODS

This application claims the benefit of U.S. Provisional Application No. 62/121,932, filed Dec. 6, 2020, the entirety of which is hereby incorporated herein by reference.

FIELD

Embodiments of the present disclosure relate generally to apparatuses and methods for circumcising male patients.

BACKGROUND

Circumcision is a surgical procedure in which some portion of the penile foreskin tissue is removed from the penis. It is the most common procedure completed on male newborns in the United States. The World Health Organization (WHO) estimates that up to 92% of newborn males are circumcised. Historically, the procedure was completed because of cultural practice or religious beliefs. There have now been several medical benefits well studied supporting the health benefits of the procedure. As of 2012 the American Academy of Pediatrics determined that the health benefits of circumcision outweighed the risks and began recommending that all newborn males be circumcised. Some of the benefits of circumcision include decreased risk for urinary tract infections, HIV transmission, penile carcinomas, and ulcerative sexually transmitted diseases. Some of the risks of having a circumcision include bleeding, penile injury, and local infections, which are common for any surgical procedure.

In the United States there are several different techniques used for circumcisions including the Gomco clamp technique, Mogen clamp technique, and Plastibell technique. The Gomco clamp is the most commonly used method in the United States. However, it was realized by the inventors of the current disclosure that problems still exist with the risk of bleeding, the accuracy of the incision, safety, and the amount of acquired skill required for the surgeon to be able to properly perform the procedure.

Consequently, there is a need for improved circumcision devices and methods. Certain preferred features of the present disclosure address these and other needs and provide other important advantages.

SUMMARY

Embodiments of the present disclosure provide an improved circumcision apparatuses and methods.

Some embodiments include a connector that permits the circumcision device to be connected by hand to, disconnected by hand from, and rotated by hand around a tissue holding member while the tissue holding member is holding penile tissue.

Additional embodiments include a cutting member (which may be referred to as a blade) that is bent at an angle. The angle of the bend may be oblique, and the blade may include a slot on either side of the bend or across the bend.

Further embodiments include at least one gripping member that extends perpendicularly to the axis about which the device rotates, while still further embodiments include at least one gripping member that is aligned with the connector at the same (or similar) location along the axis of rotation, which can assist in connection and removal of the device from a tissue holding member.

In accordance with a first aspect of embodiments of the present disclosure, a rotatable circumcision device is disclosed. The rotatable circumcision device includes a connector configured and adapted to connect by hand to a tissue holding device while the tissue holding device is holding penile tissue, rotate around the tissue holding device when the connector is connected to the tissue holding device and the tissue holding device is holding penile tissue, and disconnect by hand from the tissue holding device while the tissue holding device is holding penile tissue; and a cutting device connected to the connector, wherein the cutting device is configured and adapted to cut the foreskin of the penile tissue being held by the tissue holding device when the connector is rotated around the tissue holding device.

In accordance with another aspect of embodiments of the present disclosure, a method for manufacturing a circumcision device is disclosed. The method including forming a connector including two distal ends, an inner surface defining a connector axis, and a first retaining member, wherein the two distal ends are capable of flexing without breaking while being pressed onto an elongated member defining an elongated member axis that is parallel to the connector axis when the connector is connected to the elongated member; and forming a cutting device with a cutting edge and a second retaining member configured and adapted to interact with the first retaining member and hold the cutting device and the connector together.

In accordance with yet another aspect of embodiments of the present disclosure, a rotatable circumcision device is disclosed. The rotatable circumcision device including a cutting device configured and adapted to cut the foreskin of a patient while being held by a tissue holding device; and means for hand connecting and hand disconnecting the cutting device from a tissue holding device while the tissue holding device is holding a patient's penile tissue.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein does not necessarily address every object described herein, and each embodiment does not necessarily include each feature described. Other forms, embodiments, objects, advantages, benefits, features, and aspects of the present disclosure will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions or may have been created from scaled drawings. However, such dimensions, or the relative scaling within a figure, are by way of example, and not to be construed as limiting.

DETAILED DESCRIPTION OF THE ILLUSTRATED EMBODIMENTS

Figure 1:
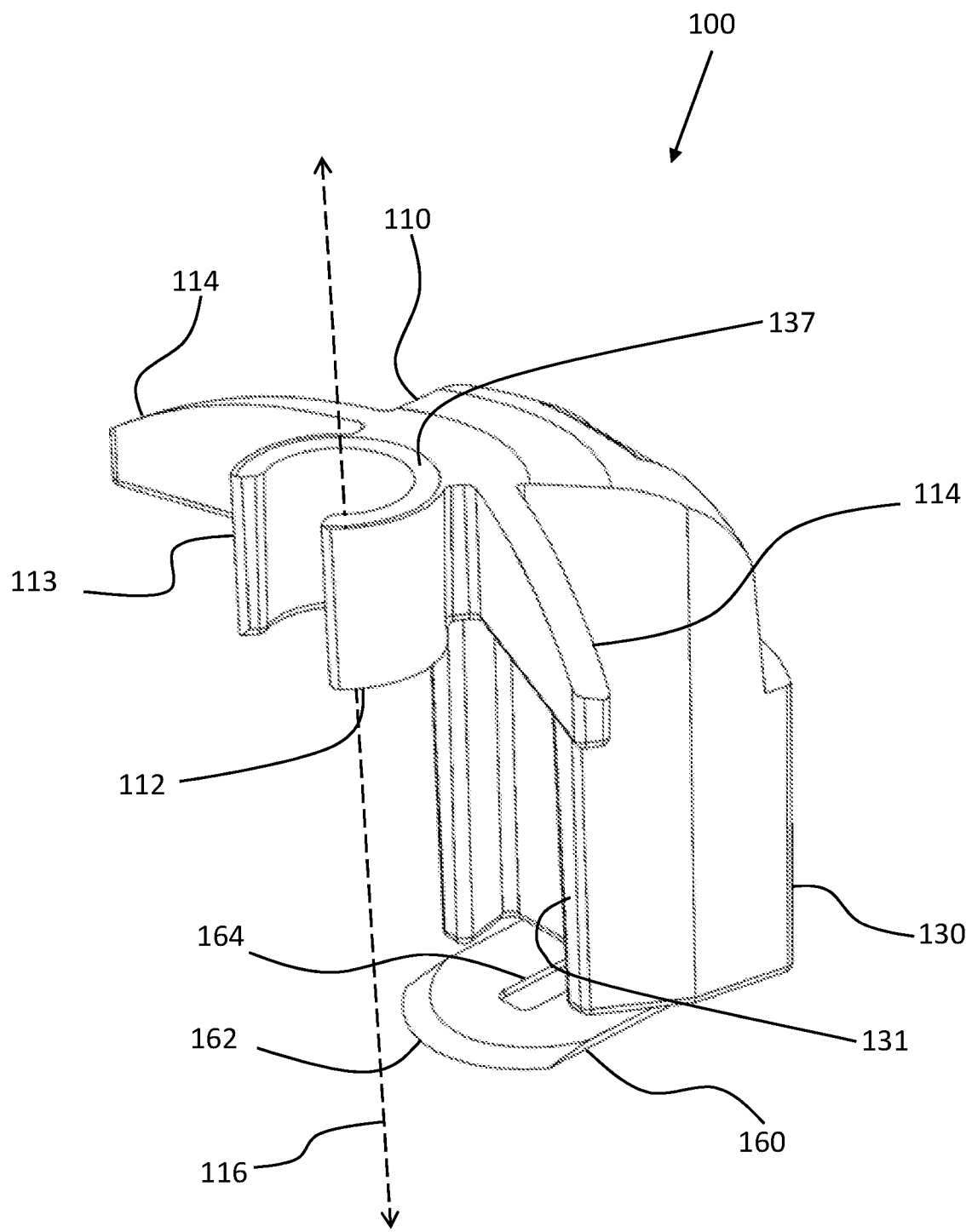
FIG. 1 is a perspective view of the front and left side of a circumcision device according to embodiments of the present disclosure.

For the purposes of promoting an understanding of the principles of the disclosure, reference will now be made to one or more embodiments, which may or may not be illustrated in the drawings, and specific language will be used to describe the same. It will nevertheless be understood that no limitation of the scope of the disclosure is thereby intended; any alterations and further modifications of the described or illustrated embodiments, and any further applications of the principles of the disclosure as illustrated herein are contemplated as would normally occur to one skilled in the art to which the disclosure relates. At least one embodiment of the disclosure is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to benefits or advantages provided by some embodiments, other embodiments may not include those same benefits or advantages, or may include different benefits or advantages. Any benefits or advantages described herein are not to be construed as limiting to any of the claims.

Likewise, there may be discussion with regards to "objects" associated with some embodiments of the present invention, it is understood that yet other embodiments may not be associated with those same objects, or may include yet different objects. Any advantages, objects, or similar words used herein are not to be construed as limiting to any of the claims. The usage of words indicating preference, such as "preferably," refers to features and aspects that are present in at least one embodiment, but which are optional for some embodiments.

Specific quantities (spatial dimensions, temperatures, pressures, times, force, resistance, current, voltage, concentrations, wavelengths, frequencies, heat transfer coefficients, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

Depicted in FIGS. 1-34 is a circumcision device 100 according to embodiments of the present disclosure. Circumcision device 100 includes a housing 110 and a cutting device 160.

The housing 110 includes a connecting portion 112, a cutting device holder 130, and optional grip assisting members, such as one or more grip assist tabs 114.

The connecting portion (or connector) 112 of housing 110 attaches to a tissue holding device (such as, tissue holding member 190, which in FIGS. 6-9 resembles a Gomco clamp) providing a secure connection between the circumcision device 100 and the tissue holding device 190 and allowing rotation of the circumcision device 100 around the tissue 900 being held by the tissue holding device 190. In the illustrated embodiment, the inner surface of the connecting portion 112 is cylindrical in shape (and in some embodiments is circularly cylindrical) with the inner surface defining an axis 116, which allows the housing 110 to rotate around the member to which the connection portion is attached and/or to rotate around axis 116. The connecting portion 112 may include two distal ends 113 defining a gap in the connecting portion 112, which facilitates attachment of the connecting portion 112 to the tissue holding device 190. For example, the connecting portion 112 may be pressed onto a portion of the tissue holding device 190 causing the distal ends 113 to initially flex outwardly then move back toward one another as the connection portion 112 becomes fully engaged with the tissue holding device 190. In some embodiments the connecting portion 112 is C-shaped.

The cutting device holder 130 of housing 110 includes a portion for retaining the cutting device 160, such as a receptacle 132 for accepting the cutting device 160. The inner surfaces of receptacle 132 may include features that assist with connecting the cutting device 160 to the housing 110. For example, the cutting device holder 130 may include devices for increasing the pressure on cutting device 160, such as pressure members 134, that may be positioned within receptacle 132 in some embodiment and can be used to help retain cutting device 160 within housing 110 and hold the cutting device 160 at a desired position and/or orientation.

Figure 3:
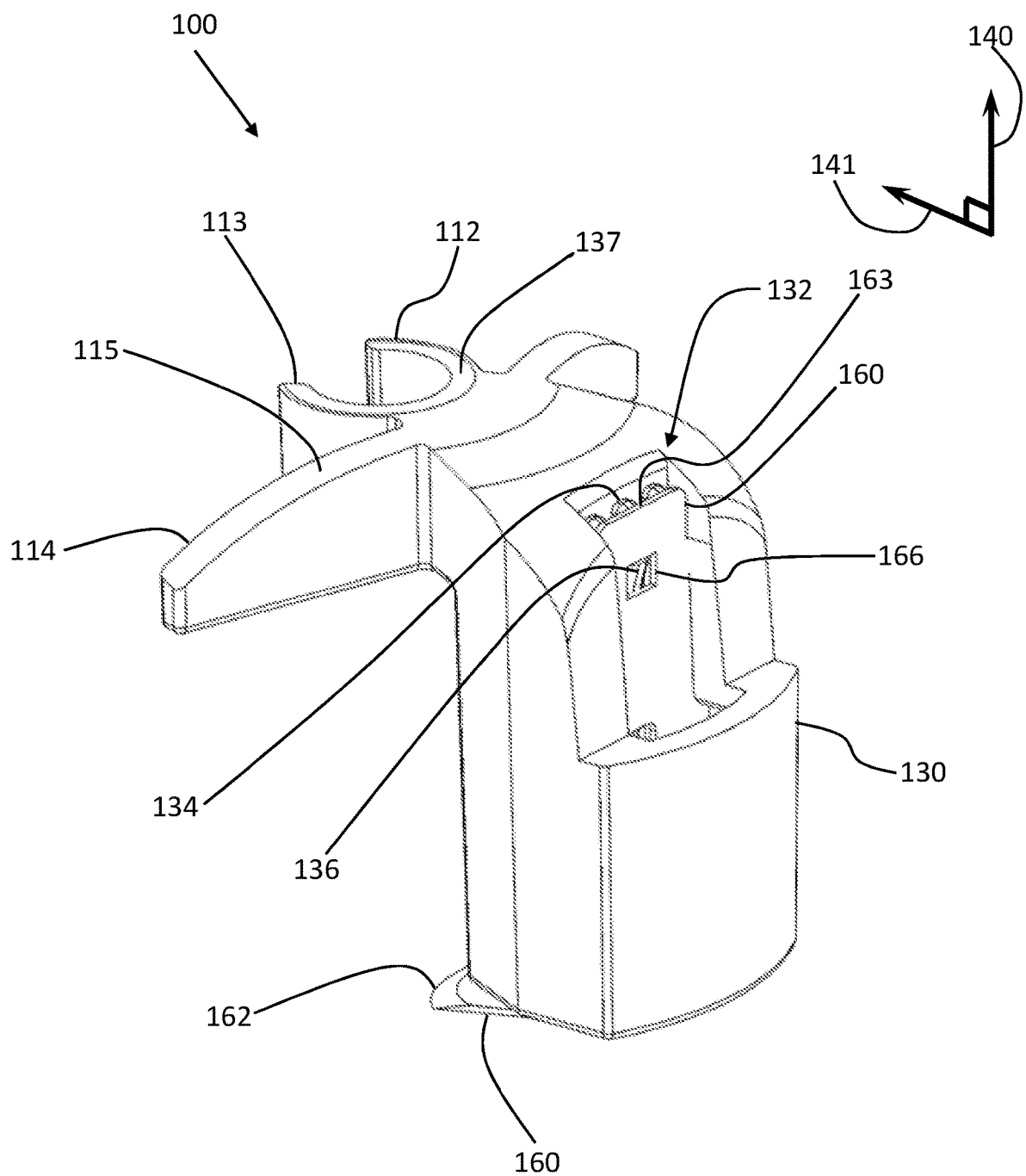
FIG. 3 is a perspective view of the back and left side of the circumcision device depicted in FIG. 1.
Figure 4:
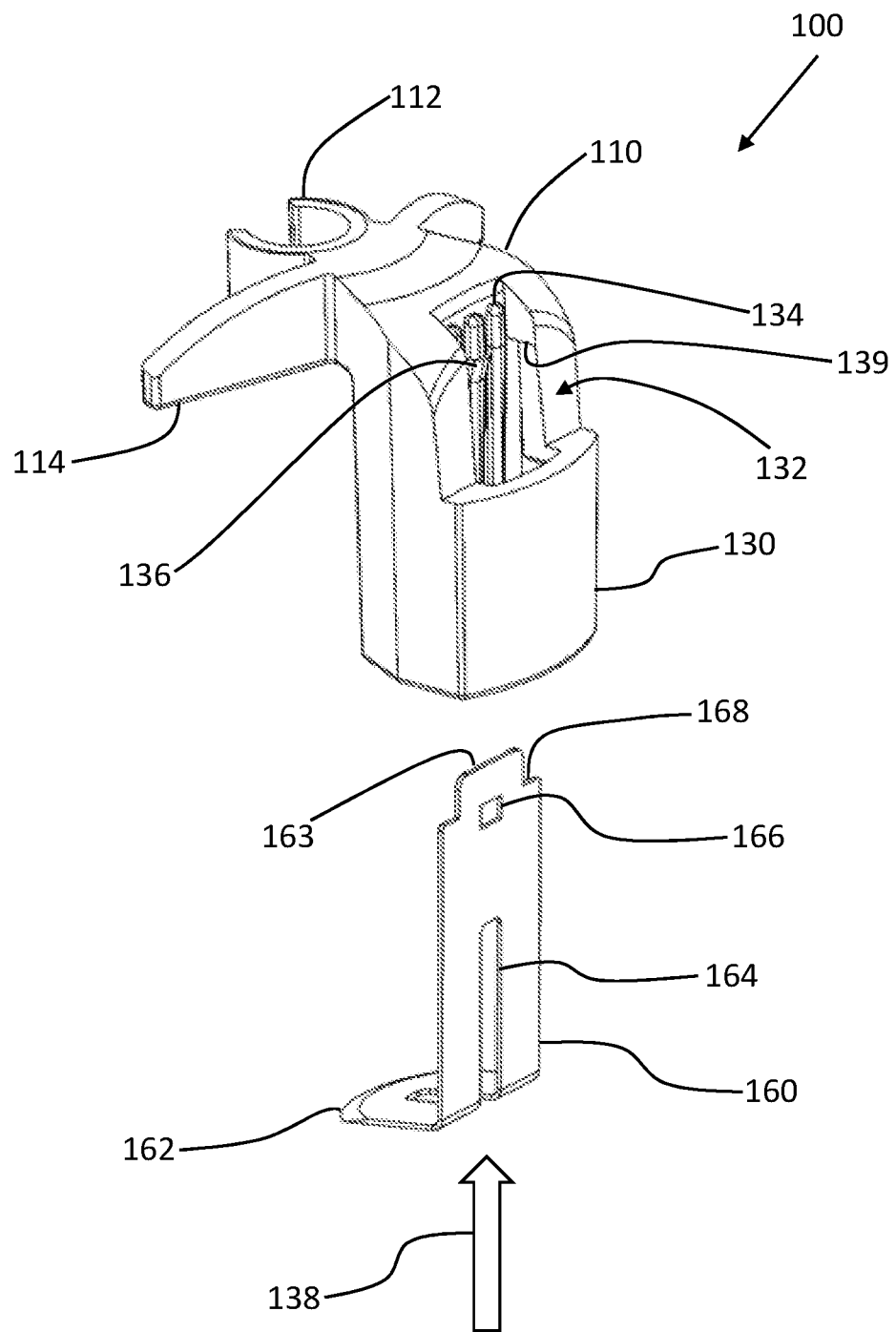
FIG. 4 is a perspective view of the back and left side of the circumcision device depicted in FIG. 3 with the cutting portion removed.

The cutting device holder 130 optionally includes one or more retention members for retaining the cutting device 160 in the cutting device holder 130. The one or more retention features (for example, one or more cutting device retaining tabs 136) may interact with one or more corresponding retention features on the cutting device 160 (for example, one or more apertures 166) to securely hold the cutting device 160 in the cutting device holder 130. At least one of the cutting device retaining tabs 136 may optionally include one or more features that assist with the insertion of the cutting device 160 into the receptacle 132 and/or engagement of the cutting device holder retention members and the cutting device 160. For example, as depicted in FIGS. 3 and 4 at least one of the cutting device retaining tabs 136 may include an angled surface or ramp upon which the upper edge 163 of the cutting device 160 presses against and slides along (which can facilitate the front surface 171 of cutting member 160 sliding along the retaining tab 136), which can deflect the cutting device 160 (such as by causing the cutting device 160 to bow around the cutting device retaining tab 136) and/or deflect the cutting device holder 130 (such as causing an optionally spring loaded cutting device retaining tab 136 to flex) until the two retention features align and engage one another (such as by the cutting device tab 136 being received in and engaging the aperture 166). In some embodiments, the one or more retention members are accessible by a user to facilitate attachment and removal of the cutting device 160 from the housing 110. For example, in the FIG. 3 the upper portion of receptacle 132 is open to allow access to the one or more retention members, for example, cutting device retaining tab 136 and aperture 166.

The one or more optional grip assisting members (for example, grip assist tabs 114) of housing 110 can provide additional grip or pressure application locations to assist a user in connecting circumcision device 100 to the tissue holding device 190 and/or assist a user with rotating circumcision device 100 around the tissue 900 being held by the tissue holding device 190. In some embodiments, such as those depicted in FIGS. 1-5, the one or more grip tabs 114 are positioned to be in alignment with the force required to mount circumcision device 100 to the tissue holding device 190. Using FIG. 3 as an example (the vertical direction 140 pointing upward and the horizontal direction 141 pointing left and slightly upward on the sheet), the one or more grip tabs 114 are aligned horizontally with the connector 112. In other words, the one or more grip tabs 114 are at the same vertical location along axis 116 (see, FIG. 3) as the connector 112. To mount connector 112 of housing 110 to the tissue holding device 190, a horizontal force is required. With the grip tabs 114 aligned horizontally with the connector 112, application of a horizontal force to the grip tabs 114 results in a horizontal force being applied to the connector 112. If the grip tabs 114 were at a different vertical position than the connector 112, such as if the tabs were located near the bottom of housing 100, application of a horizontal force to the grip tabs 114 would result in a twisting motion at the connector 112 making it more difficult to attach the housing 110 to the tissue holding device 190.

In additional embodiments, the grip assist tabs 114 extend horizontally (which in FIG. 3 can be in direction 141 and/or in a direction perpendicular to both directions 141 and 140, and in FIG. 1 can be in a direction that is perpendicular to axis 116) outward from the connector 112, which can help the user in rotating the housing 110 about the vertical axis defined by the connector 112 when the connector 112 (and therefore the housing 110) are connected to the tissue holding device 190. In still further embodiments the upper surface 115 of the one or more grip assist tabs 114 may be positioned below the upper surface 137 of housing 110 and/or shaped to avoid interference with the tissue holding device 190 as the housing 110 is rotated.

The cutting device 160 includes a cutting edge 162 designed to cut the tissue of the patient, and in particular the foreskin tissue of the patient's penis. In some embodiments, the shape of cutting edge 162 is rounded to facilitate smooth cutting of the tissue. However, in alternate embodiments the amount of rounding of the cutting edge 162 is different to change the angle at which the cutting edge 162 intersects the tissue as the cutting device 160 is rotated, and is some embodiments the cutting edge 162 is straight. As can be seen in FIG. 1, the portion where the cutting edge 160 intersects both sides of the cutting device 160 may also be shaped to present less than a 90 degree angle in order to avoid the end of the cutting edge 162 inadvertently catching of the tissue as the cutting device 160 is rotated.

Figure 5:
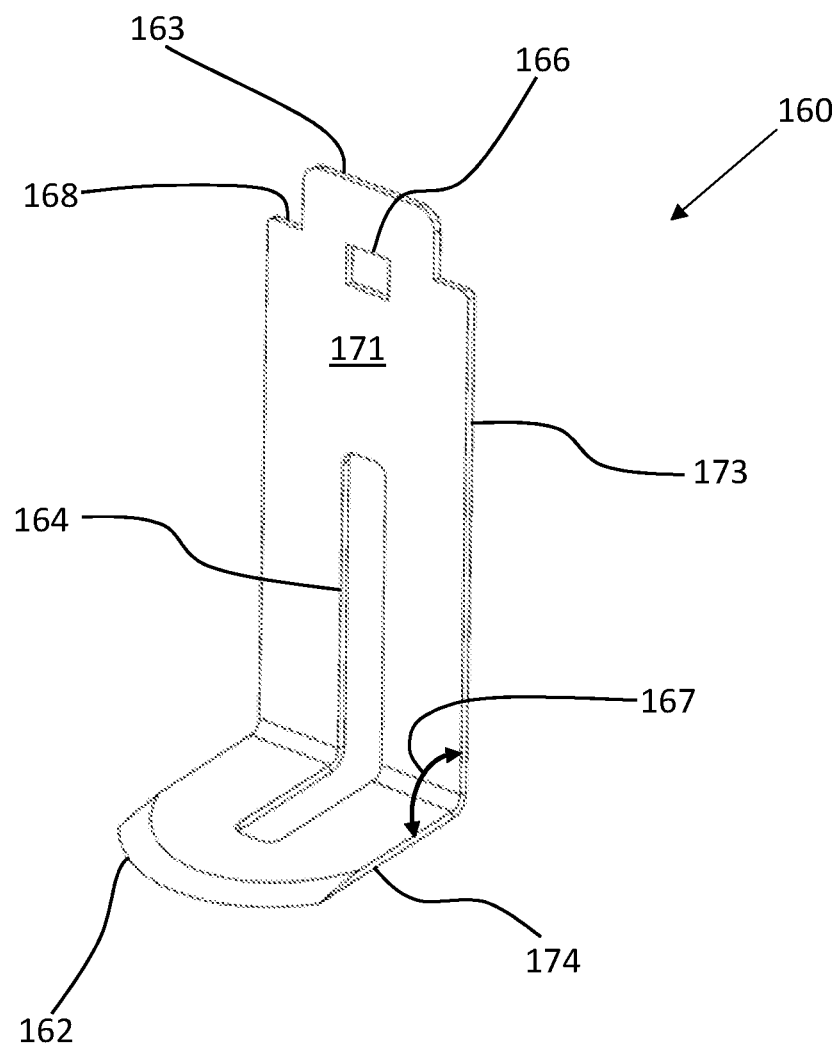
FIG. 5 is a perspective view of the front and left side of the cutting portion depicted in FIG. 4.
Figure 6:
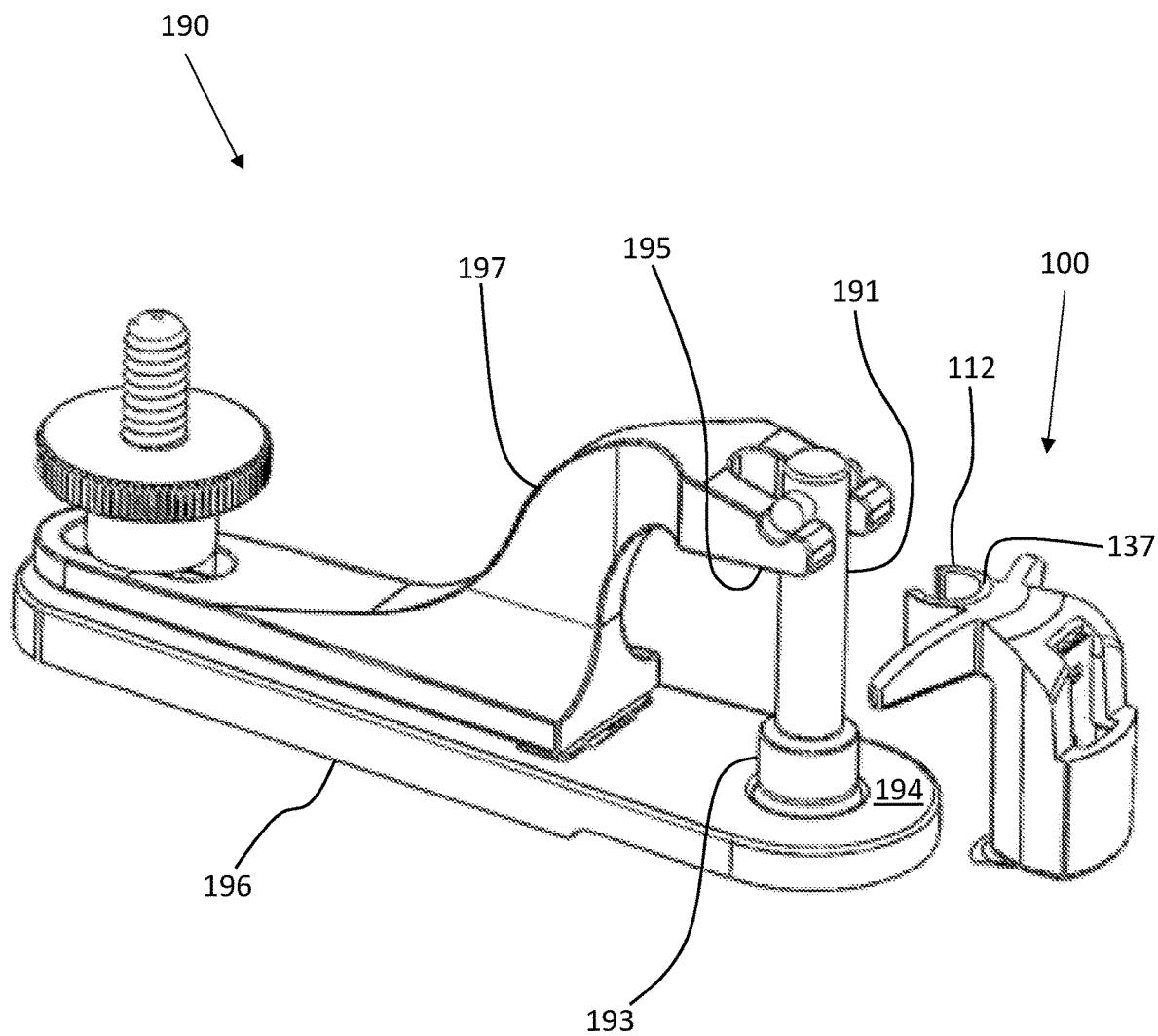
FIG. 6 is a perspective view of the back and left side of the circumcision device depicted in FIG. 1 positioned in a pre-mounting position to a tissue holding device according to embodiments of the present disclosure.

The cutting device 160 optionally includes one or more force adjustment features and/or retention features. In the illustrated embodiment the one or more force adjustment features include one or more apertures and/or slots 164 in the cutting device 160. The one or more slots 164 may be included in the vertical portion 173, the horizontal portion 174, and/or extend between the vertical portion 173 and the horizontal portion 174 as depicted in FIG. 5. The one or more slots 164 reduce the amount of material in vertical portion 173 and/or horizontal portion 174, which can help reduce the amount of force required to flex/bend the vertical portion 173 and/or the horizontal portion 174. Another benefit of the one or more slots 164 is that they reduce the amount of material required to produce each cutting device 160 and can also add aesthetic features to the cutting device 160. The one or more retention features in cutting device can include one or more apertures 166 that can engage with one or more retention features on the housing 110 as discussed above.

Figure 7:
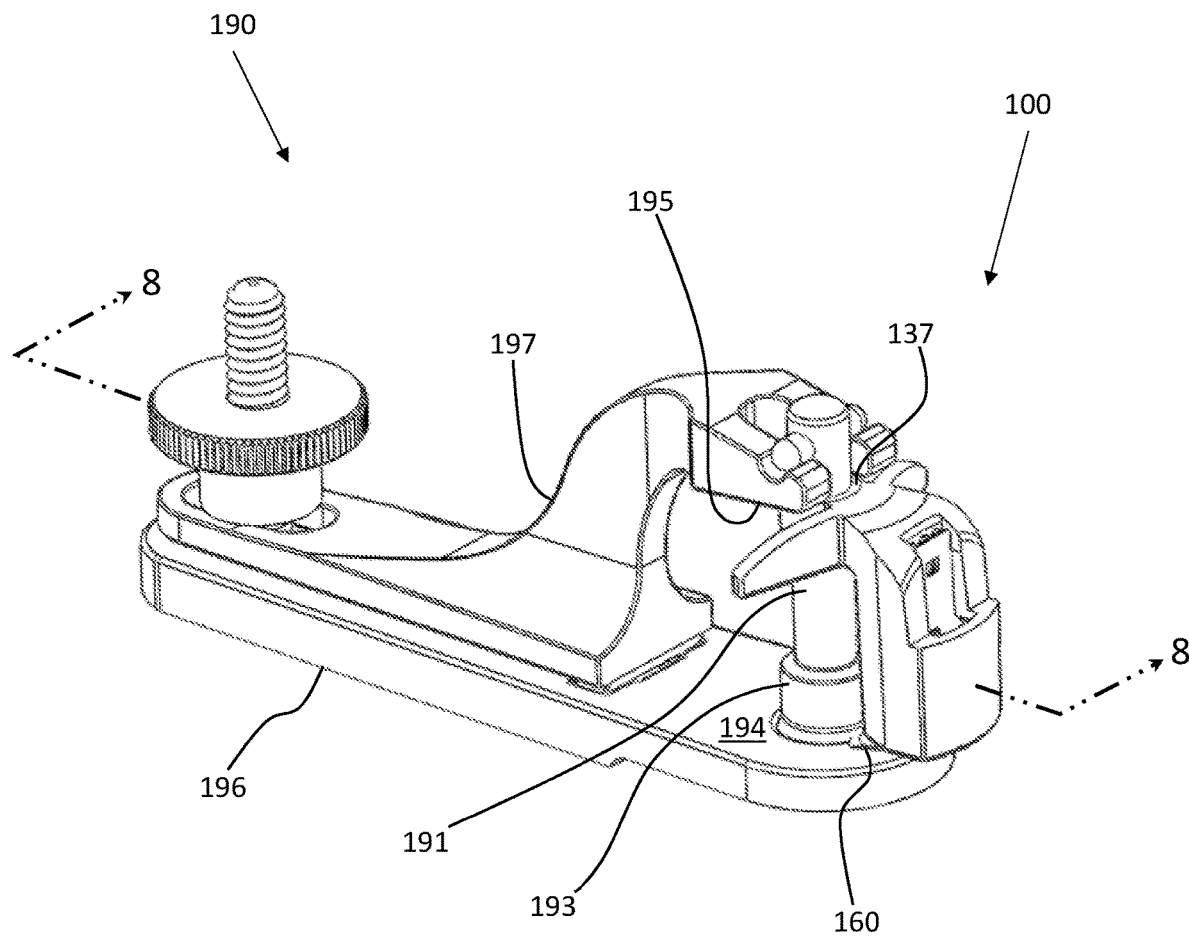
FIG. 7 is a perspective view of the back and left side of the circumcision device depicted in FIG. 1 mounted to the tissue holding device depicted in FIG. 6.
Figure 8:
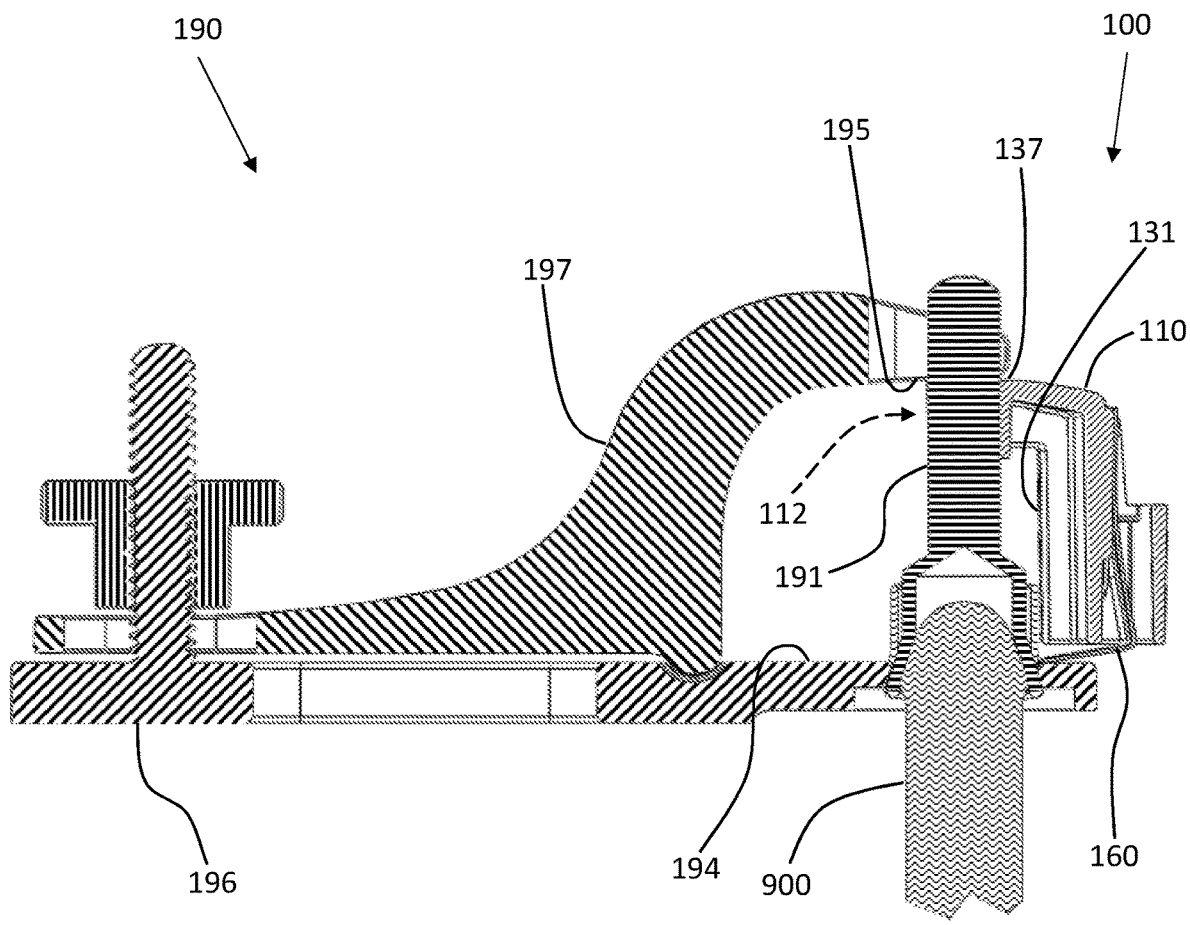
FIG. 8 is a sectional view of the circumcision device mounted to the tissue holding device as depicted in FIG. 7 taken along line 8-8.

The vertical portion 173 and the horizontal portion 174 of the cutting device 160 are oriented at an angle 167 with respect to one another. The angle 167 can assist in securely holding the circumcision device 100 to the tissue holding device 190, such as by applying a vertical spring force of the cutting device 160 acting on a surface of the tissue holding device 190 (such as upper surface 194, see FIG. 7) to hold the upper surface 137 of housing 110 against another surface of to the tissue holding device 190 (such as lower surface 195, see FIG. 7). As depicted in FIGS. 5, 7 and 8, the angle 167 may exceed 90 degrees. In some embodiments angle 167 is at least 90 degrees and at most 131 degrees, while in additional embodiments angle 167 is at least 91 degrees and at most 120 degrees, and in still further embodiments angle at least 100 degrees and at most 110 degrees.

To attach the cutting device 160 to the housing 110, a user can orient cutting device 160 and housing 110 as depicted in FIG. 4 and move the cutting device 160 in direction 138 until the cutting device 160 is inserted into receptacle 132. As the cutting device 160 is inserted into receptacle 132 pressure members 134 press against the front surface 171 of the cutting device 160 and increase the pressure and friction on the cutting device 160. As cutting device 160 is inserted into the receptacle 132, the upper edge 163 of the cutting device 160 contacts the sloped/ramped surface of the cutting device retaining tab 136. As the cutting device 160 continues to move into receptacle 132, the upper edge 163 of cutting device 160 deflects cutting device retaining tab 136 and/or the cutting device 160 deflects/flexes around the retaining tab 136. The cutting device retaining tab 136 and/or the cutting device 160 remain in their deflected states until the complementary retaining feature 166 of the cutting device 160 aligns with the cutting device retaining tab 136 and the cutting device retaining tab 136 is inserted into the aperture 166. At around the same insertion distance as when the cutting device retaining tab 136 engages the aperture 166 of the cutting device 160, the insertion stop 168 of the cutting device 160 reaches a complementary stopping surface 139 in cutting device holder 130, which inhibits the cutting device 160 from being inserted farther into the receptacle 132. Once the cutting device 160 is securely connected to the cutting device holder 130 (such as by being securely fastened within the receptacle 132), the circumcision device 100 may be used to cut the foreskin tissue of a patient.

Figure 9:
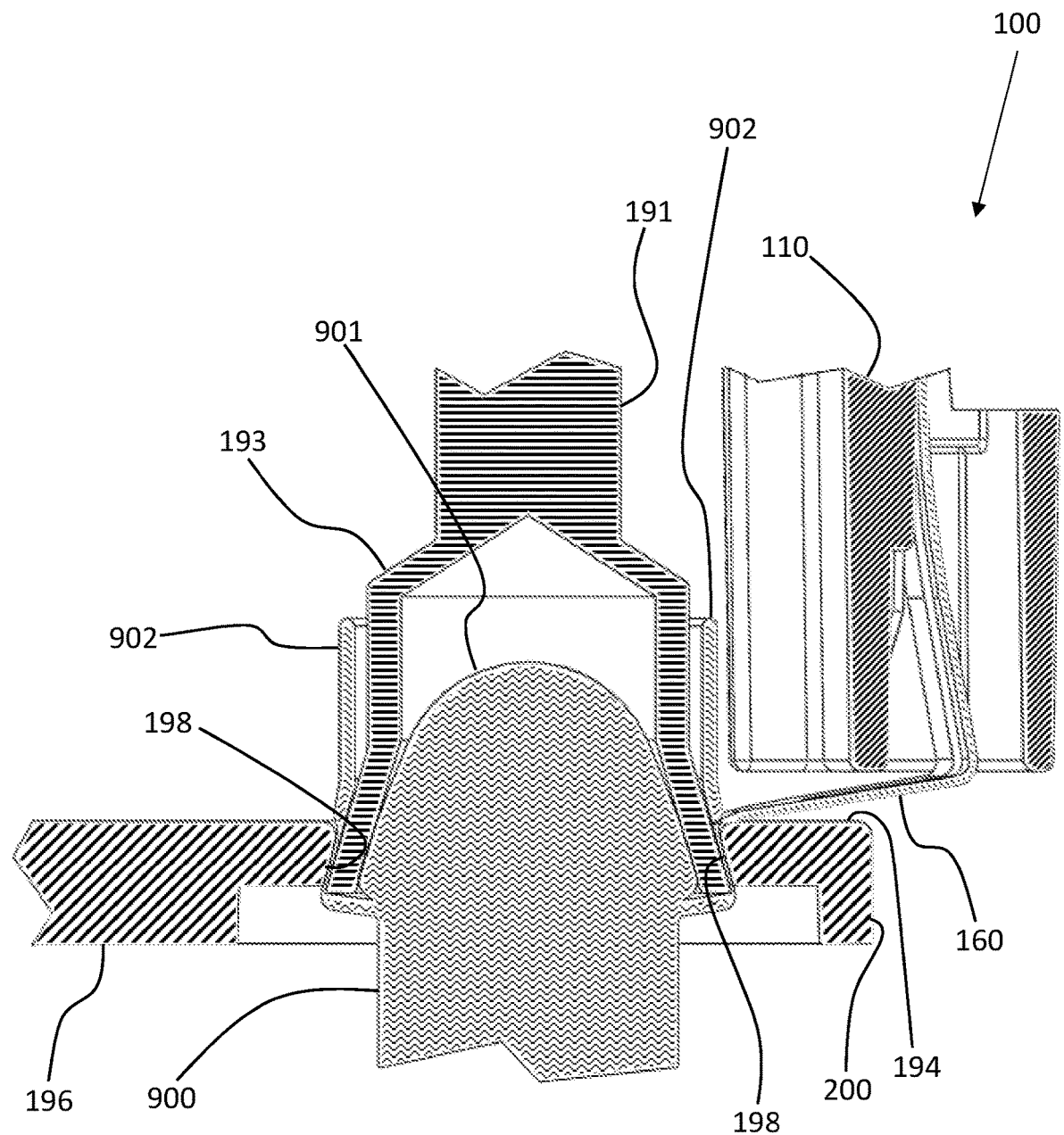
FIG. 9 is a partial view of the circumcision device mounted to the tissue holding device as depicted in FIG. 8.

In use, a user (such as an obstetrician or surgeon) will attach a tissue holding member, such as the example tissue holding device 190, to a patient's penis. Using FIG. 9 as an example, the user will insert the glans 901 of the patient's penis into the bell 193 and pull the foreskin 902 around the outside of the bell 193. The vertical extension 191 is then inserted through an aperture 198 in the base plate 196, and the base plate 196 is moved down around the bell 193 and the foreskin 902 surrounding the bell 193 until the foreskin 902 is positioned between the side wall of aperture 198 and the outer surface of the bell 193 as depicted in FIGS. 8 and 9. Of note is that FIGS. 8 and 9 depict the circumcision device 100 attached to the tissue holding device, which is typically not the case until after the tissue holding device is attached to the patient's penis.

After the tissue holding device 190 is attached to the patient, the user will typically attach the circumcision device 100 to the tissue holding device 190. For example, the housing 110 of the circumcision device 100 can be moved into a pre-engagement orientation with the tissue holding device 190 as depicted FIG. 6. The housing 110 may then be moved toward the tissue holding device 190 until the connector 112 of the housing 110 engages with the tissue holding device 190. For example, as depicted in FIG. 7 the connector 112 engages with the tissue holding device 190 when the housing 110 embraces the vertical extension 191 of the bell 193 of tissue holding device 190. As the distal ends 113 of the connector 112 contact the vertical extension 191, the user generally needs to apply additional force in order to move the distal ends 113 and the two sides of the connector 112 apart and continue moving the connector 112 onto the vertical extension 191.

In embodiments with one or more grip assist tabs 114, it may be helpful for the user to press on the grip assist tabs 114 to help connect connector 112 to the vertical extension 191 of the tissue holding device 190. In embodiments where the grip assist tabs are aligned with the force required to connect the connector 112 to the vertical extension 191, such as in the embodiments depicted in FIGS. 6 and 7, accidental rotation and misalignment of the connector 112 and the vertical extension 191 is minimized resulting in an easier process for connecting connector 112 to the vertical extension 191.

As the connector 112 is pushed farther onto the vertical extension 191 and the distal ends 113 of the connector 112 pass the widest portion of vertical extension 191, the separated distal ends 113 of the connector 112 will begin moving together, which can result in the connector 112 (and the rest of the circumcision device 100) snapping onto the vertical extension 191 and fully attaching the circumcision device 100 to the tissue holding device 190.

As the connector 112 attaches to the vertical extension 191, the cutting device 160 may contact the upper surface 194 of base plate 196. In these situations, the cutting device 160 may slide along the upper surface 194 of base plate 196 before reaching the bell 193 and/or the tissue 900 to be cut (for example, foreskin 902), which will be positioned outside of the bell 193 as depicted in FIGS. 8 and 9.

Once the circumcision device 100 is properly connected to the tissue holding member 190, the user can rotate circumcision device 100 around the patient's tissue and cut the foreskin 902. If additional pressure of the cutting device 160 on the tissue is desired, the user may press on housing 110, such as by pushing perpendicularly to axis 116 on, for example, the grip assist tab 114 and/or the cutting device holder 130 (such as toward the bottom of the cutting device holder 130). With the cutting device 160 registered against the upper surface 194 of the base plate 196, the cutting edge 162 creates a straight and smooth incision through the foreskin 902. Moreover, if the cutting edge 162 does not completely cut through the foreskin 902 on a single pass, the user may continue rotating the circumcision device 100 around the patient's tissue until the foreskin 902 is completely removed from the patient's penis.

Figure 2:
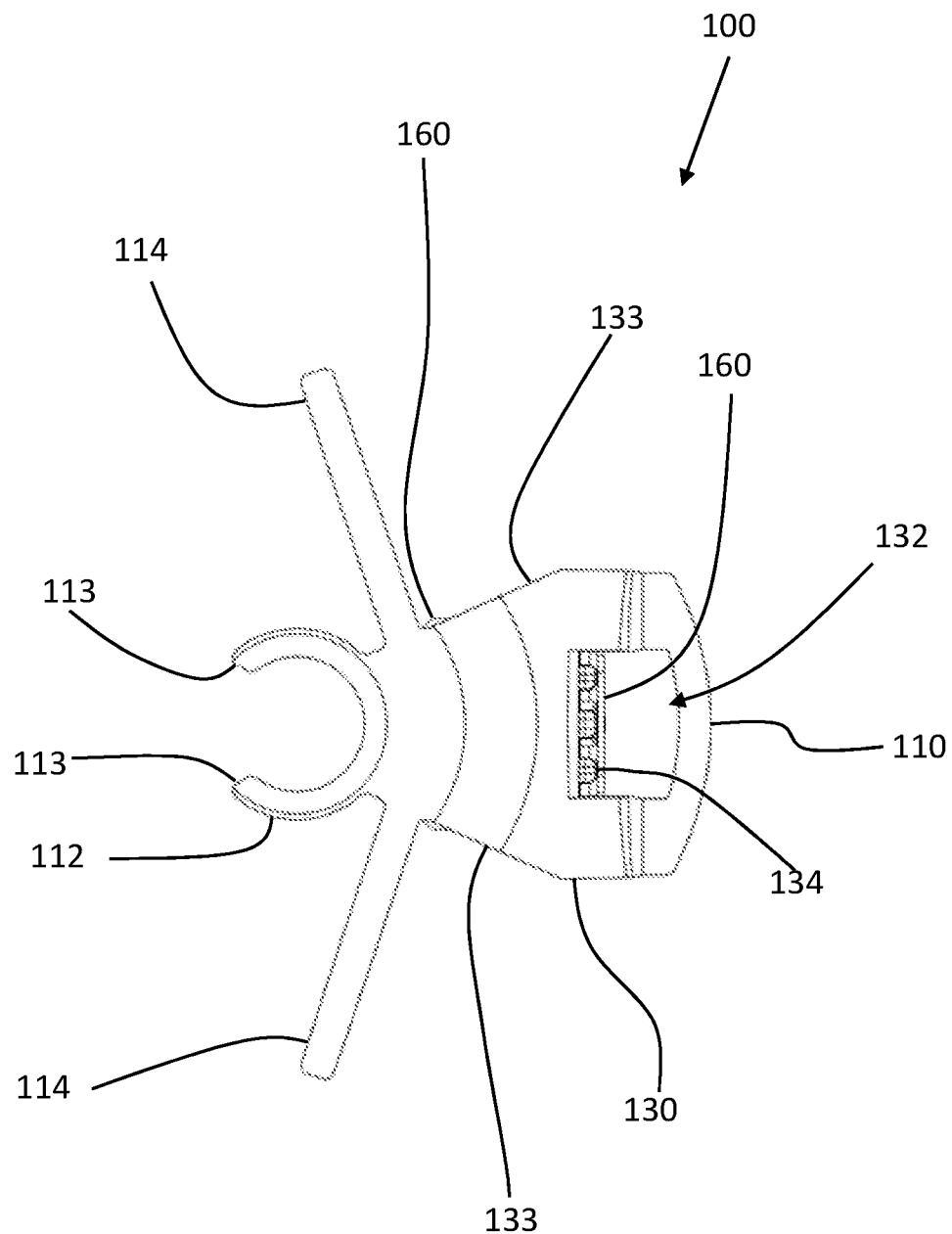
FIG. 2 is a top plan view of the circumcision device depicted in FIG. 1.

When the user is finished cutting through the foreskin 902, the user can remove the circumcision device 100 from the tissue holding member 190. To accomplish this the user has options. One option is for the user to grasp the grip assist tabs 114 and pull the connector 112 off of and away from the vertical extension 191 of the tissue holding member 190. Another option is for the user to grasp the outer surfaces 133 of housing 110 (at least portions of which may be tapered to enhance grasping as depicted in FIG. 2), pull the lower portion of housing 110 (the portion near cutting edge 162) outwardly, and rotate the connector 112 off of the vertical extension 191 of the tissue holding member 190.

Once the circumcision device is removed from the tissue holding member 190, the user can either dispose of the circumcision device 100 as assembled with the housing 110 and the cutting device connected together, or may remove the cutting device (such as by, for example, depressing cutting device retaining tab 136 and/or pulling outwardly on the upper edge 163 of the cutting device 160 (see, FIG. 3)) and disposing of the cutting device 160 separately.

In some embodiments the distance 169 between the tip of the cutting edge 162 and the upper surface 137 of the housing 110 is greater than the distance 192 between the lower surface 195 of the arm 197 of the tissue holding member 190 and the upper surface 194 of the base plate of the tissue holding member 190. See, FIG. 10 for example representations of distances 169 and 192. In these embodiments the horizontal portion 174 of the cutting device 160 acts as a spring to push against the upper surface 194 of the base plate and hold the upper surface 137 of the housing 110 against the lower surface 195 of the arm 197.

In these embodiments the angle 167 between the vertical portion 173 and the horizontal portion 174 of the cutting device 160 (see, FIG. 5) is greater than what is needed to place the cutting edge 162 of the cutting device 160 in contact with the upper surface 194 of the tissue holding number 190 when the housing 110 is properly connected to the tissue holding member 190. In some embodiments the horizontal portion 174 of the cutting device 160 deflects slightly exerting an upward force on the housing 110 of the circumcision device 100 helping hold the circumcision device 100 in a secure vertical position with respect to the tissue holding device 190. See, for example, FIG. 7. For example, the upward force generated by the horizontal portion 174 of the cutting device 160 can hold the upper surface 137 of the circumcision device 100 against the lower surface 195 of the tissue holding number 190.

The amount of pressure exerted by the horizontal portion 174 onto the upper surface 194 can be controlled by varying, for example, one or more of the following: the angle 174 between the horizontal portion 174 and the vertical portion 173 of the cutting device 160; the material used for manufacturing the cutting device 160; the presence, location, number and size of the one or more slots 164; the angle 167 at which the horizontal portion 174 is oriented with respect to the vertical portion 173 of the cutting device 160; and the orientation of the vertical portion 173 adjacent the bend in the cutting device 160 where the vertical portion 173 transitions into the horizontal portion 174 when the cutting device 160 is mounted to the cutting device holder 130 of housing 110 (in other words, the orientation at which the cutting device holder 130 holds the cutting device 160, and in particular the lower part of the vertical portion 173 of the cutting device 160).

Figure 10:
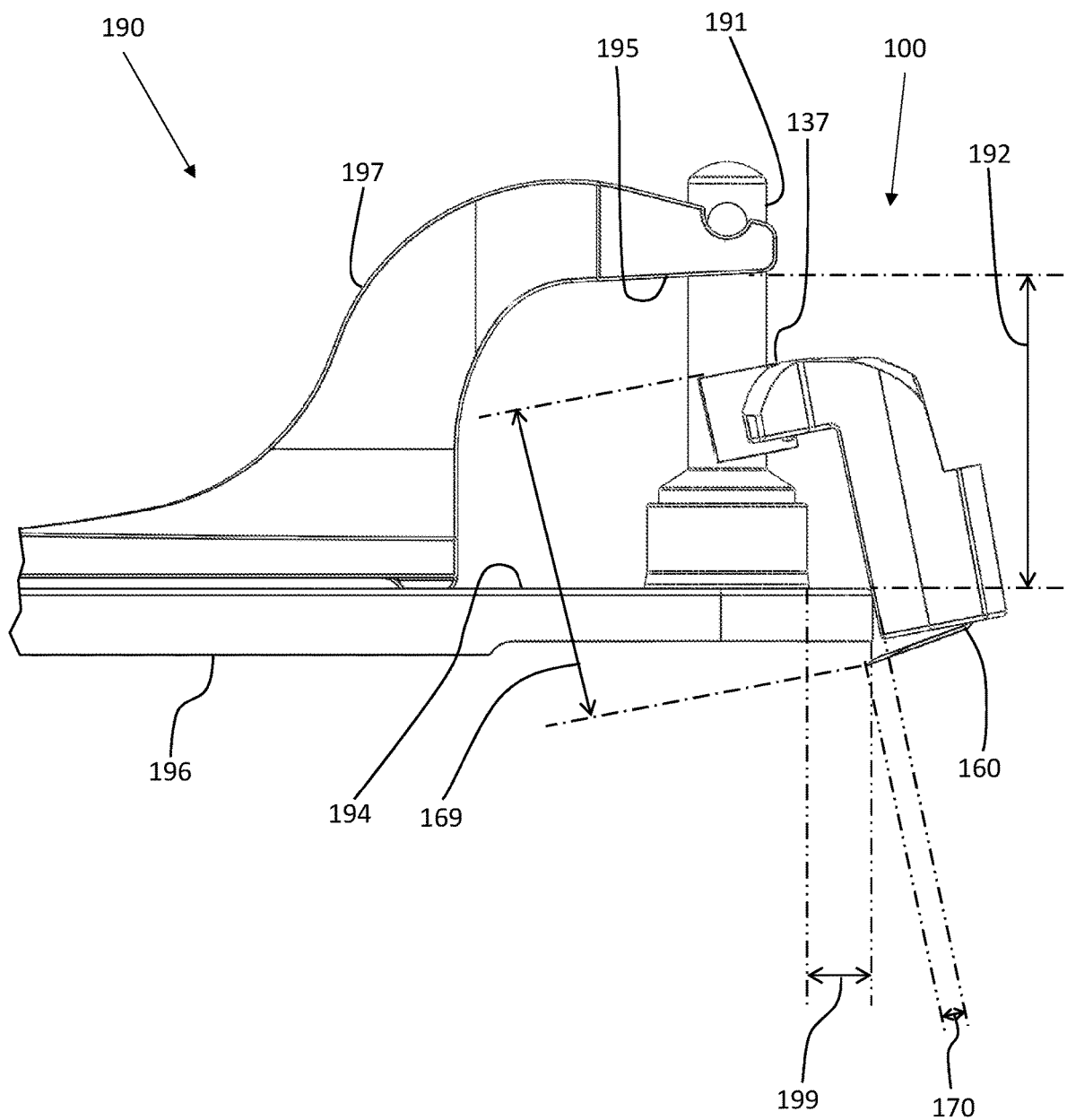
FIG. 10 is a left elevational view of the circumcision device depicted in FIG. 1 incorrectly mounted to a tissue holding device according to embodiments of the present disclosure.
Figure 11:
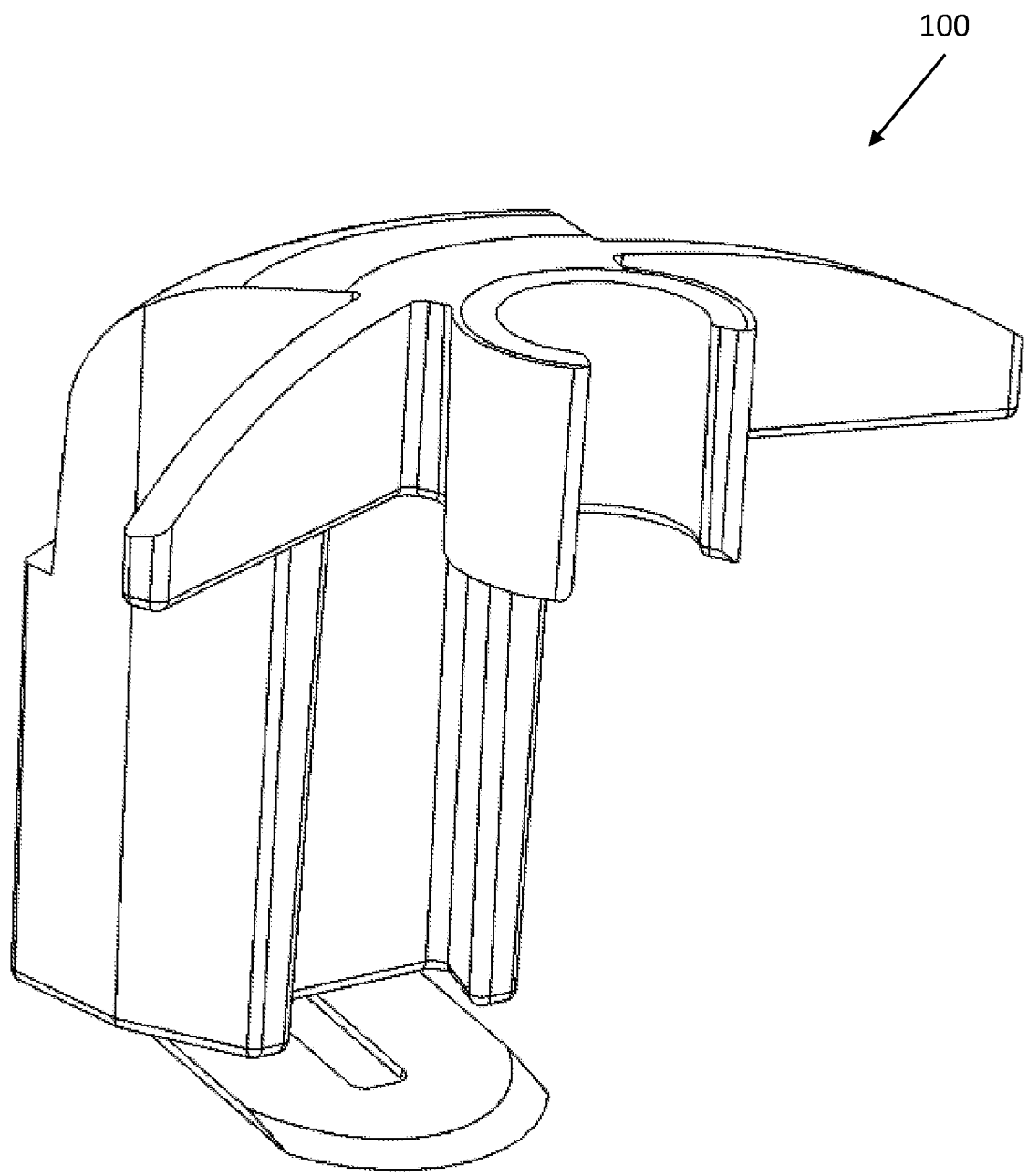
FIG. 11 is a perspective view of the front and right side of the circumcision device depicted in FIG. 1.
Figure 12:
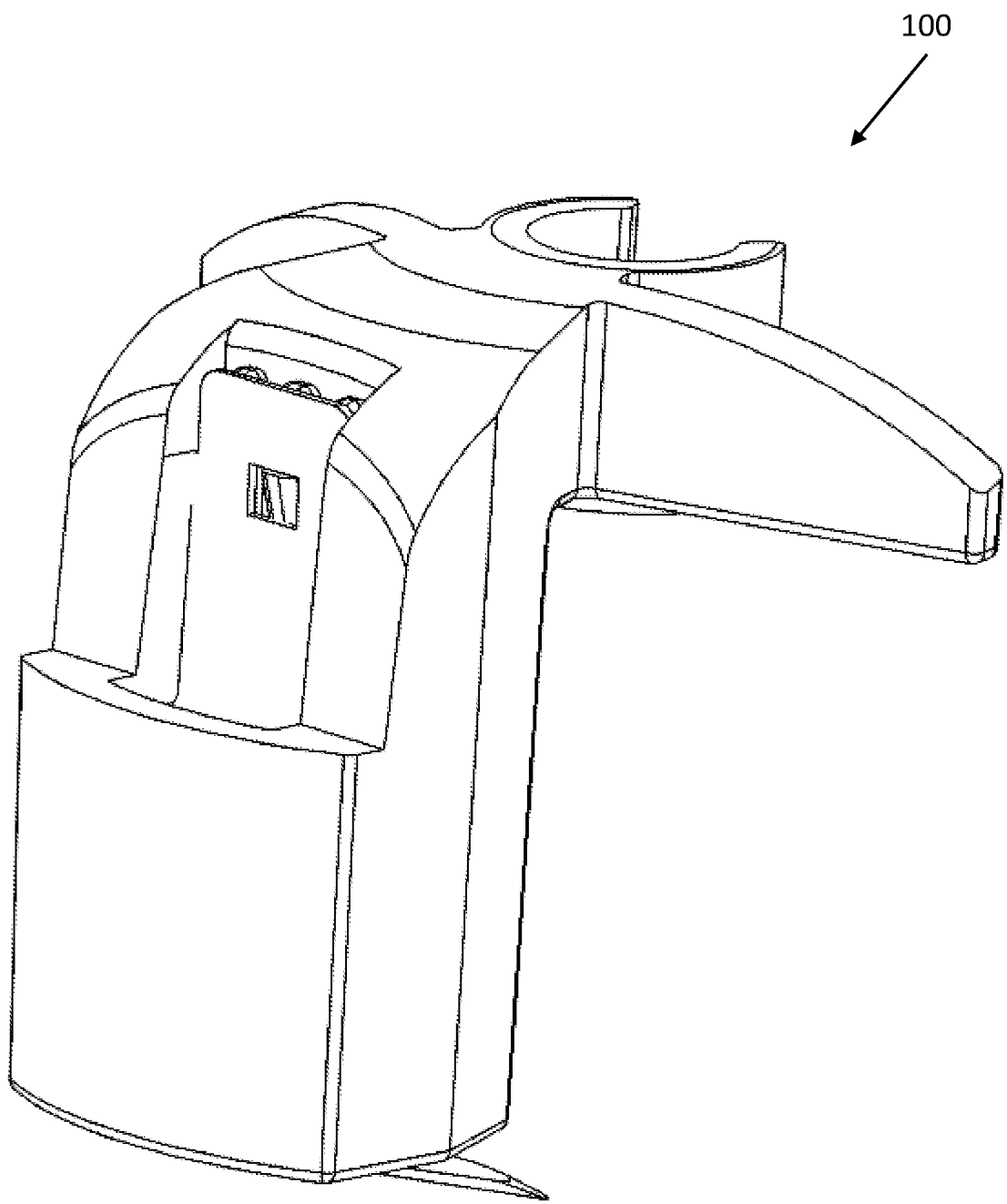
FIG. 12 is a perspective view of the back and right side of the circumcision device depicted in FIG. 1.
Figure 13:
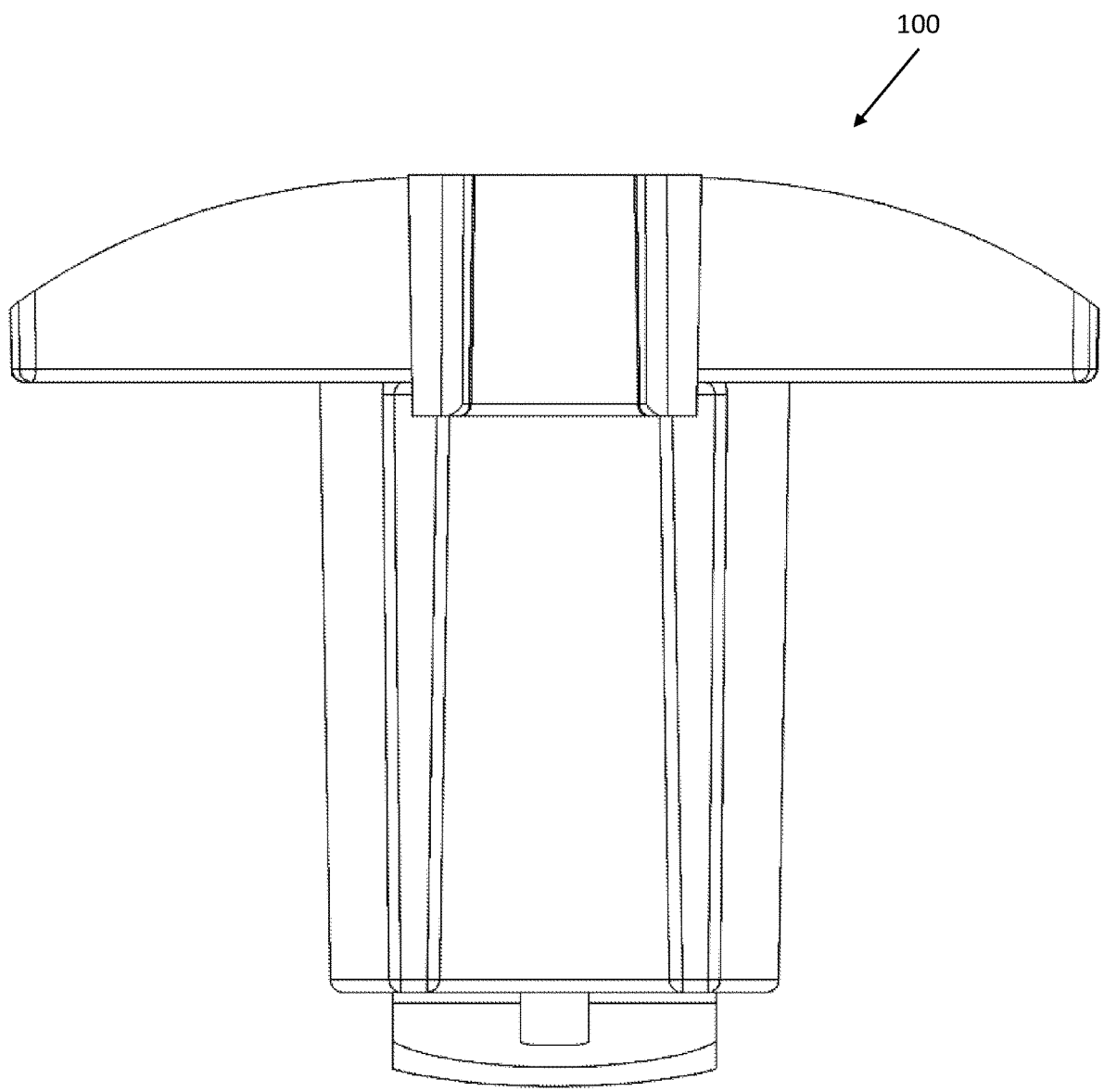
FIG. 13 is a front elevational view of the circumcision device depicted in FIG. 1.
Figure 14:
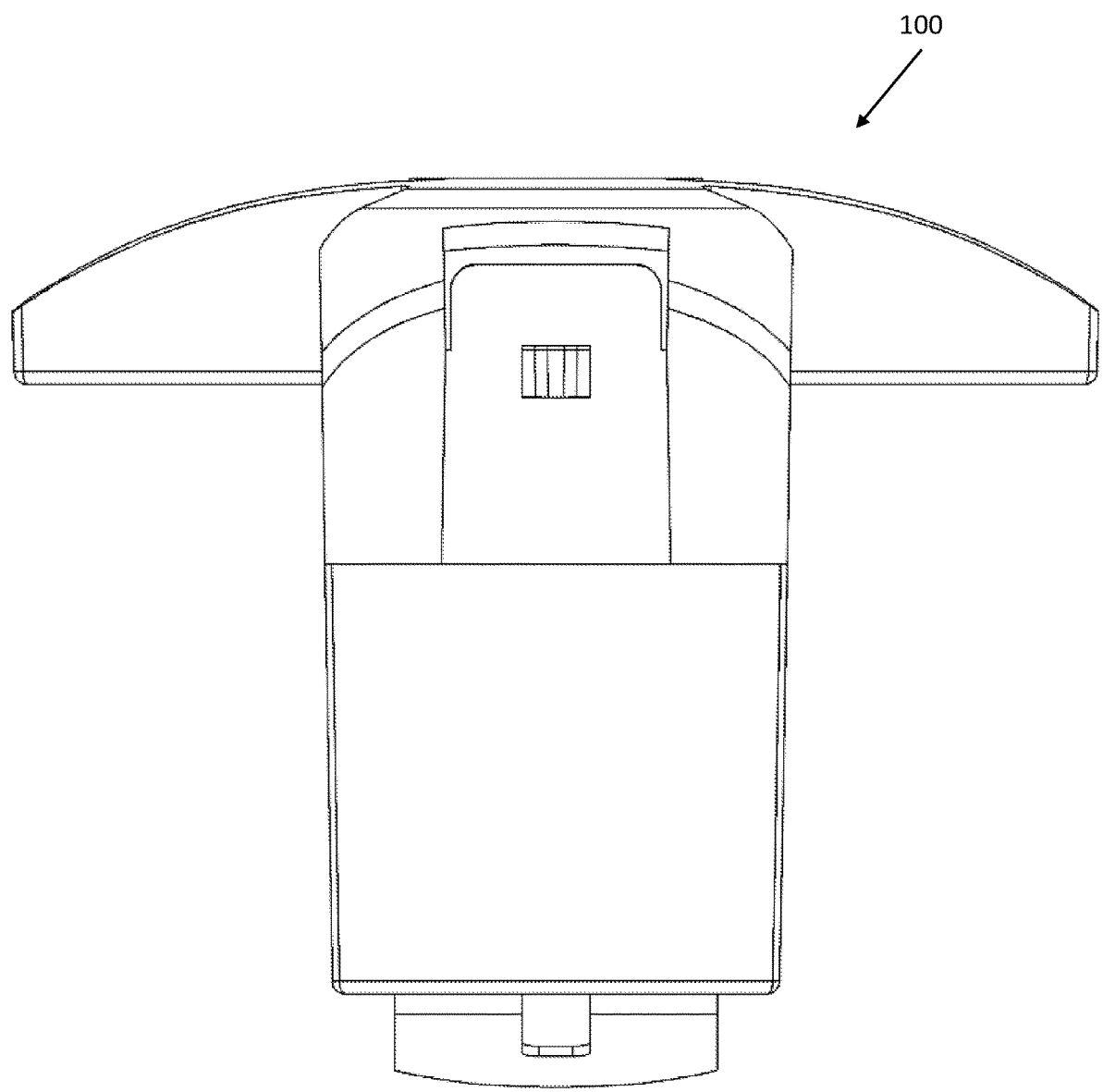
FIG. 14 is a back elevational view of the circumcision device depicted in FIG. 1.
Figure 15:
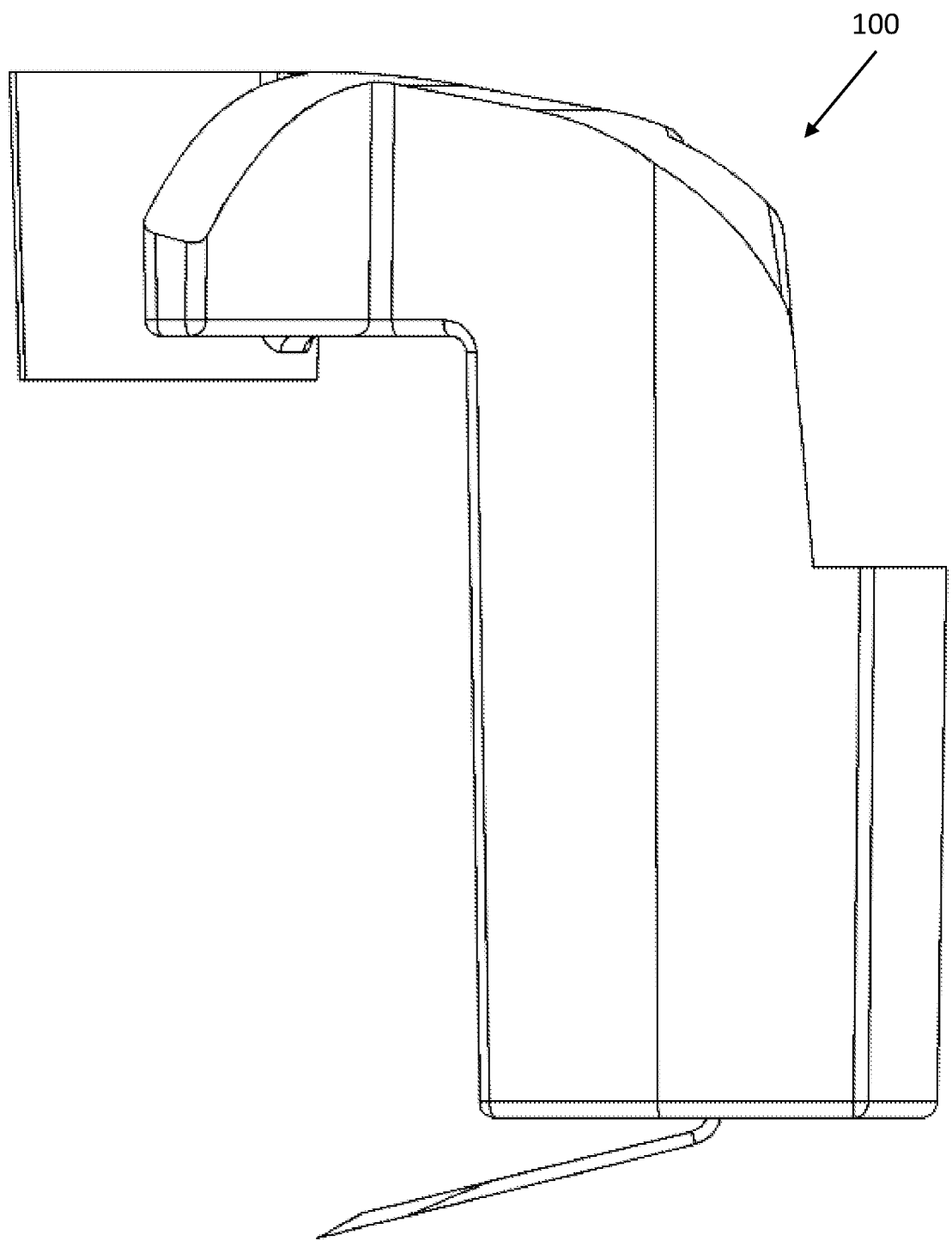
FIG. 15 is a left side elevational view of the circumcision device depicted in FIG. 1.
Figure 16:
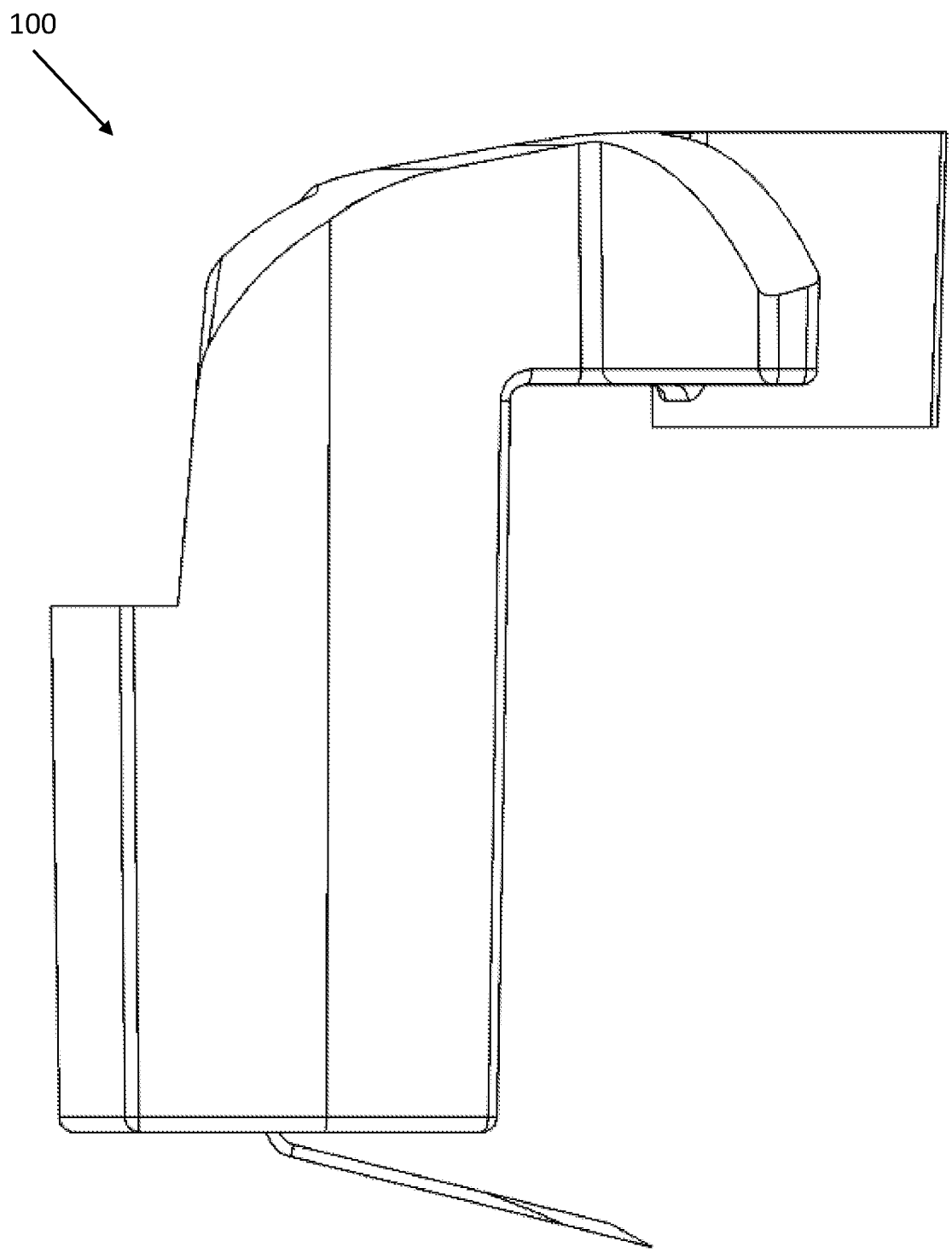
FIG. 16 is a right side elevational view of the circumcision device depicted in FIG. 1.
Figure 17:
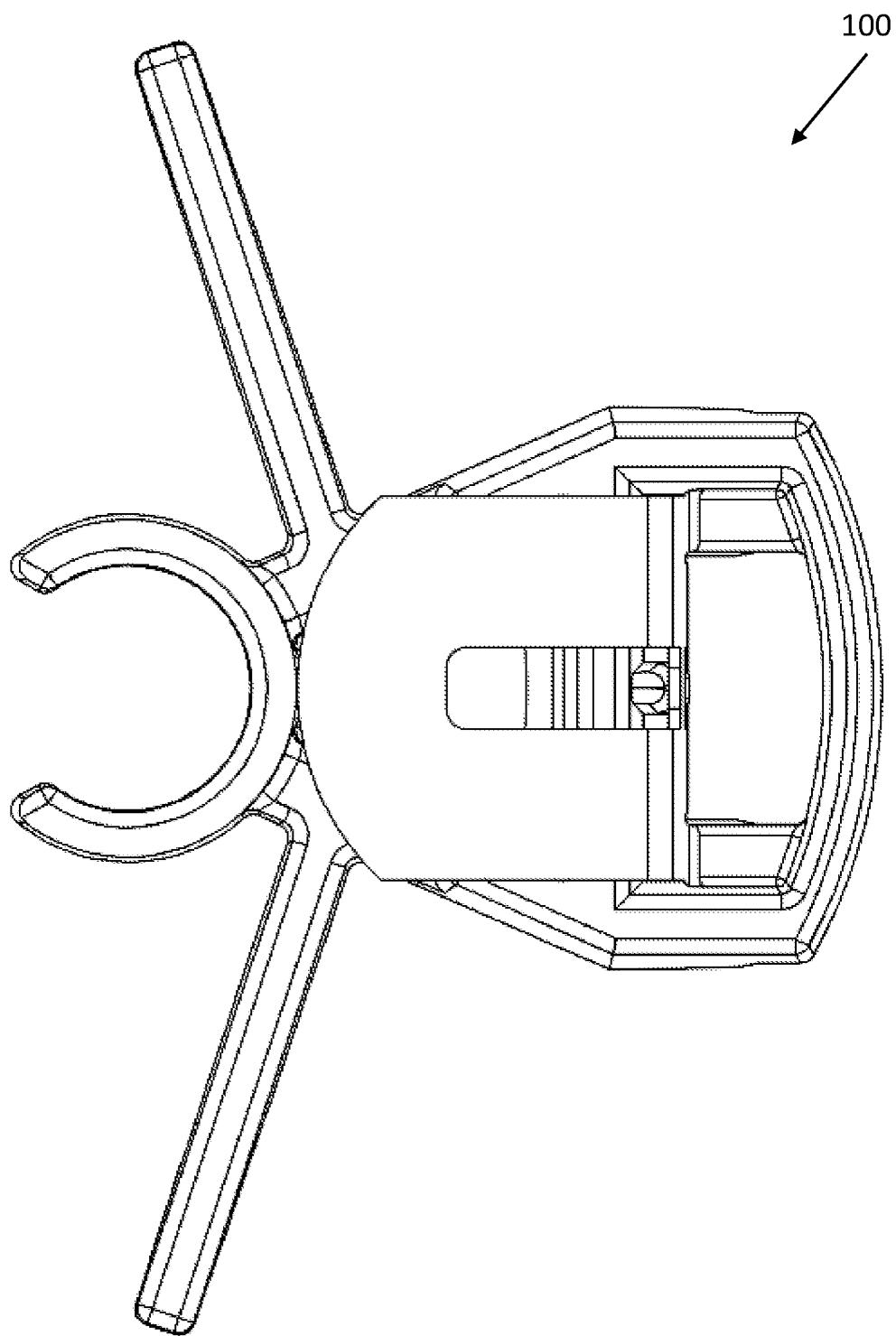
FIG. 17 is a bottom plan view of the circumcision device depicted in FIG. 1.
Figure 18:
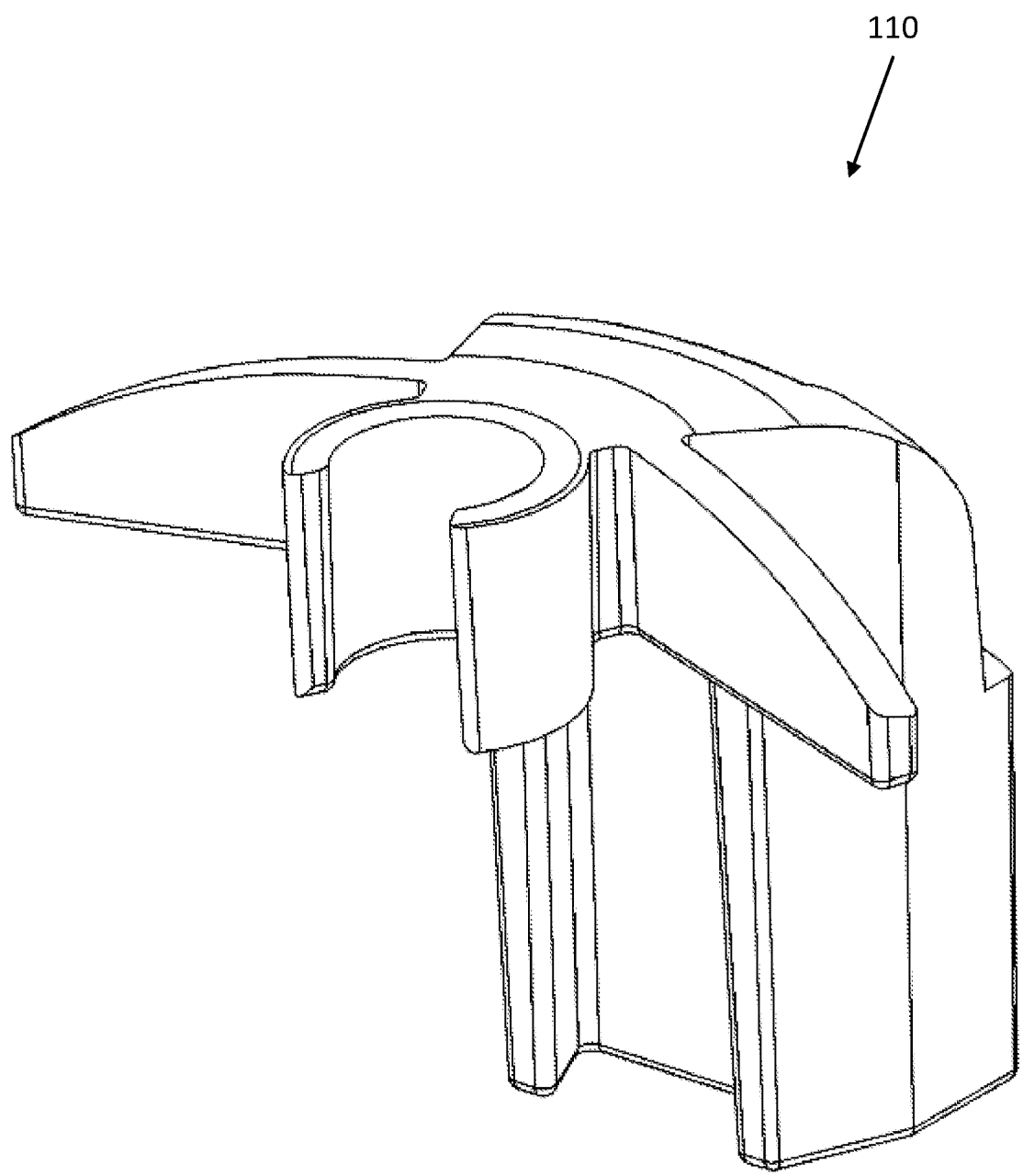
FIG. 18 is a perspective view of the front and left side of the circumcision device housing depicted in FIG. 1.
Figure 19:
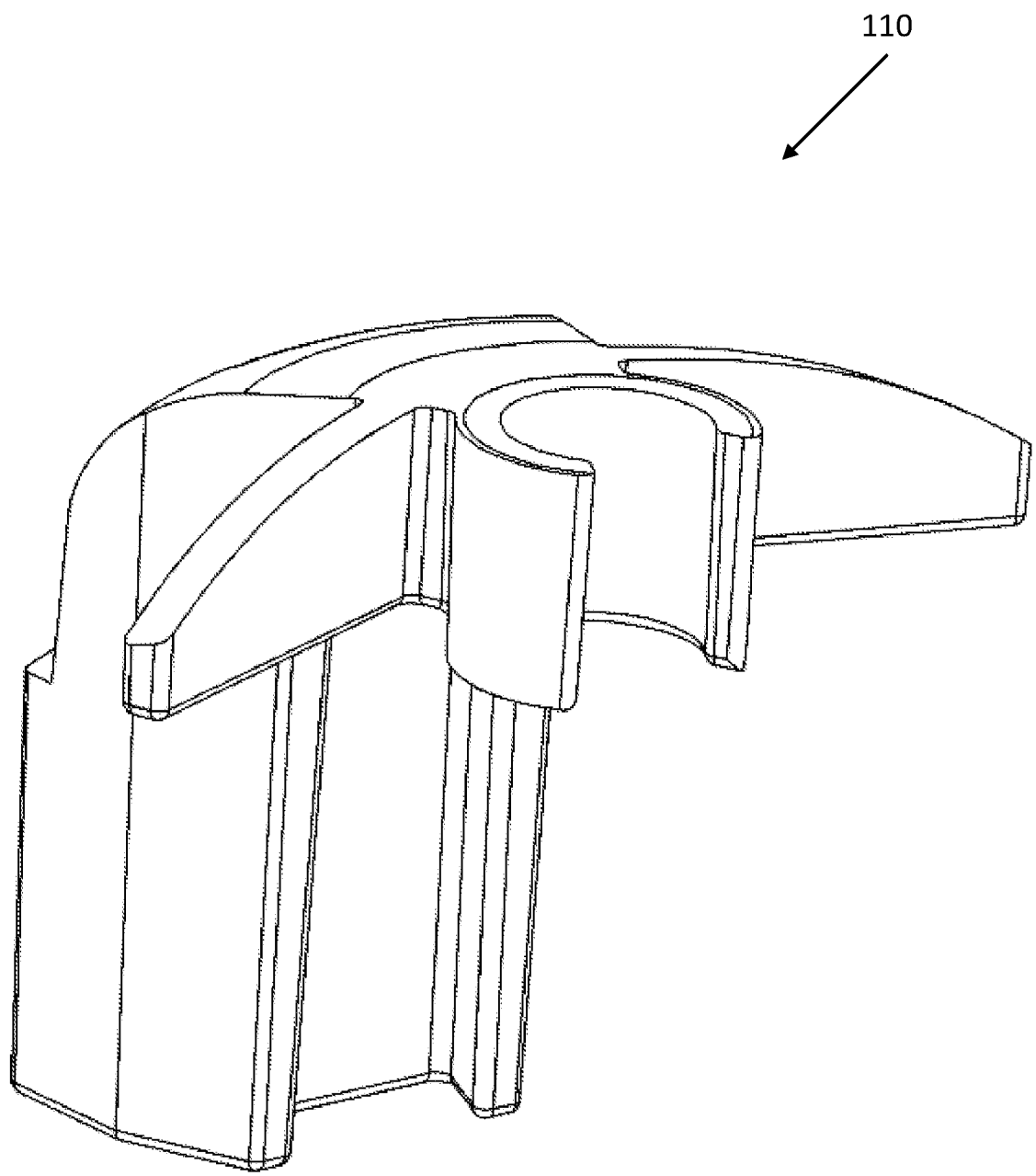
FIG. 19 is a perspective view of the front and right side of the circumcision device housing depicted in FIG. 1.
Figure 20:
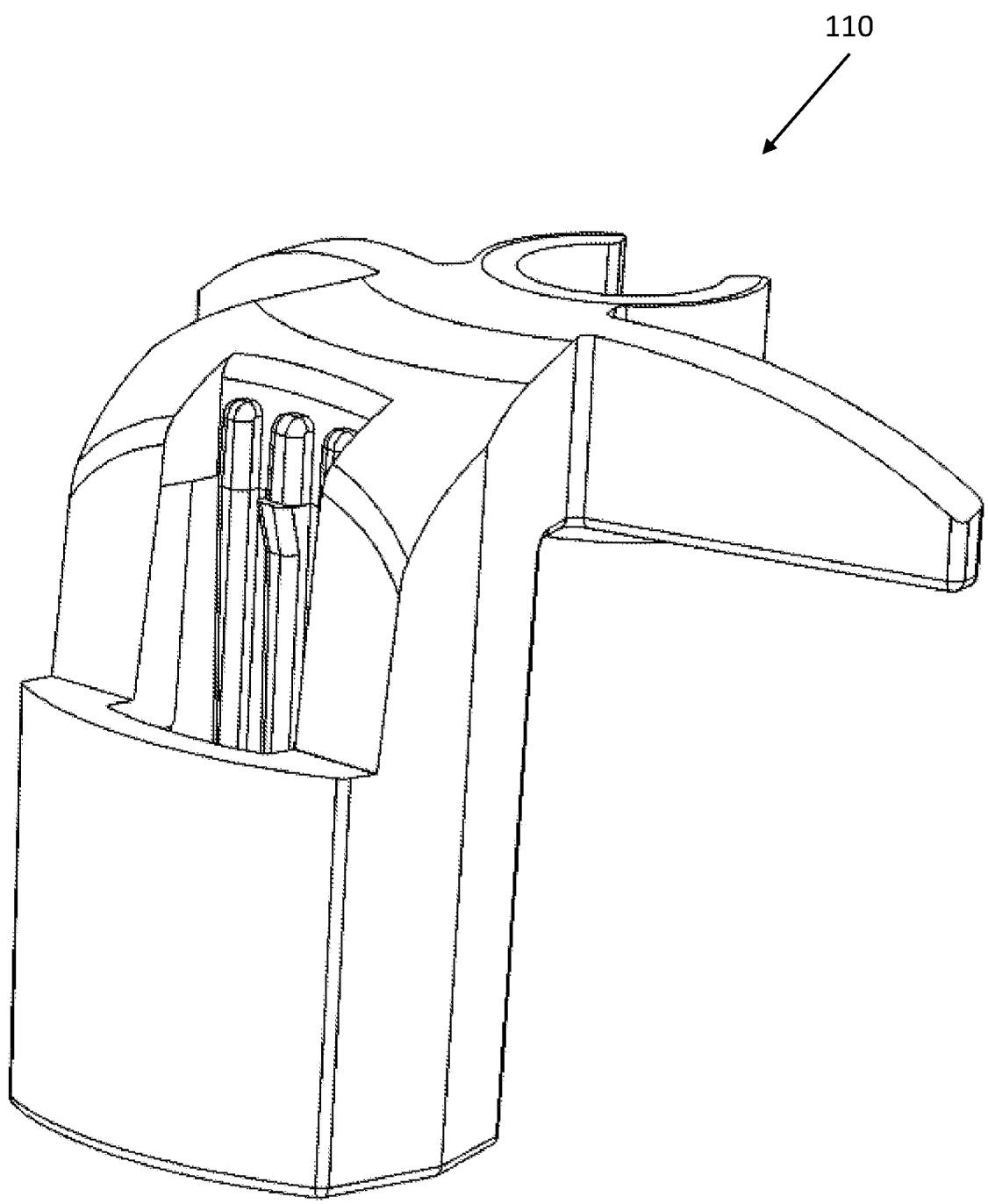
FIG. 20 is a perspective view of the back and right side of the circumcision device housing depicted in FIG. 1.
Figure 21:
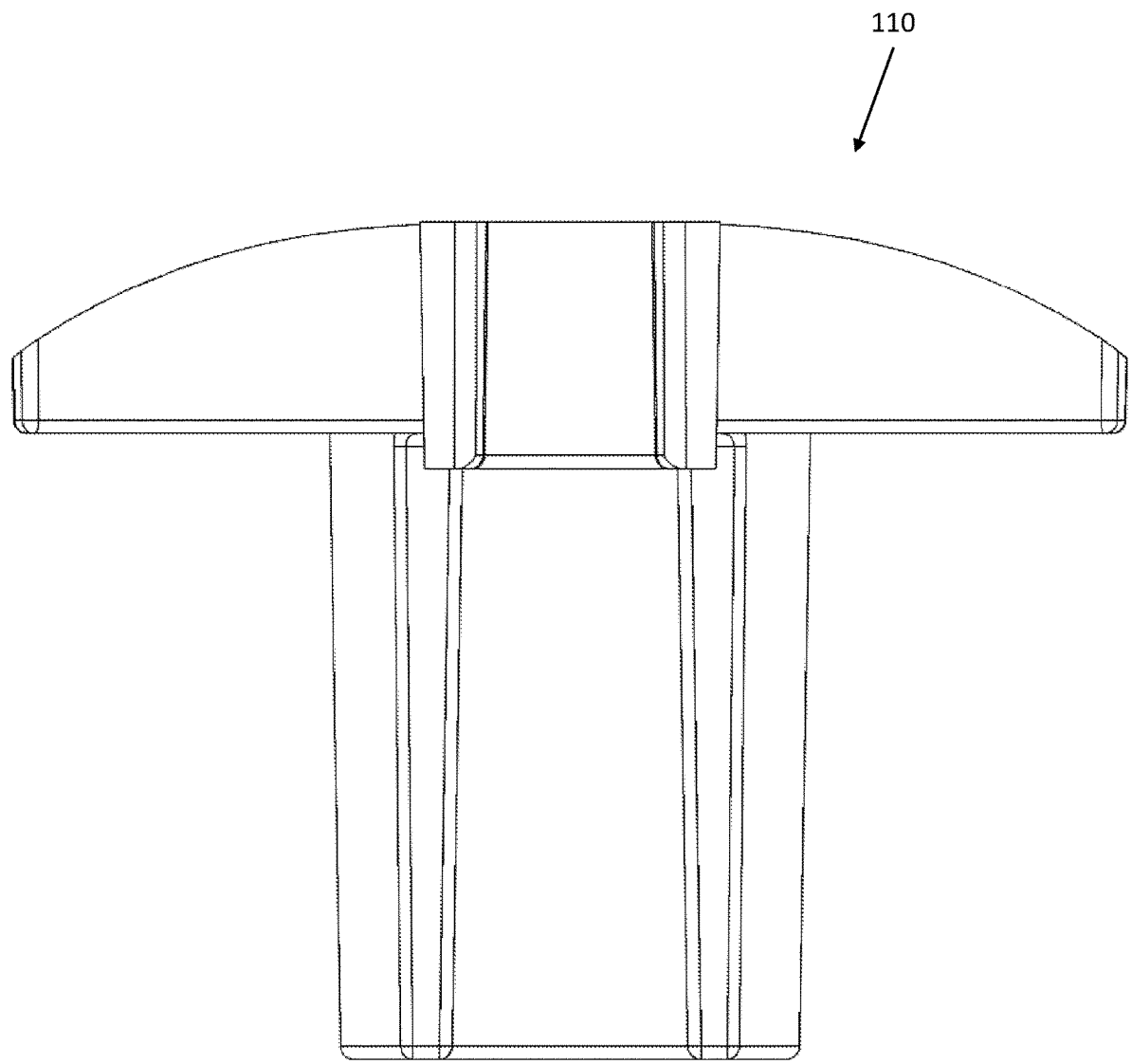
FIG. 21 is a front plan view of the circumcision device housing depicted in FIG. 1.
Figure 22:
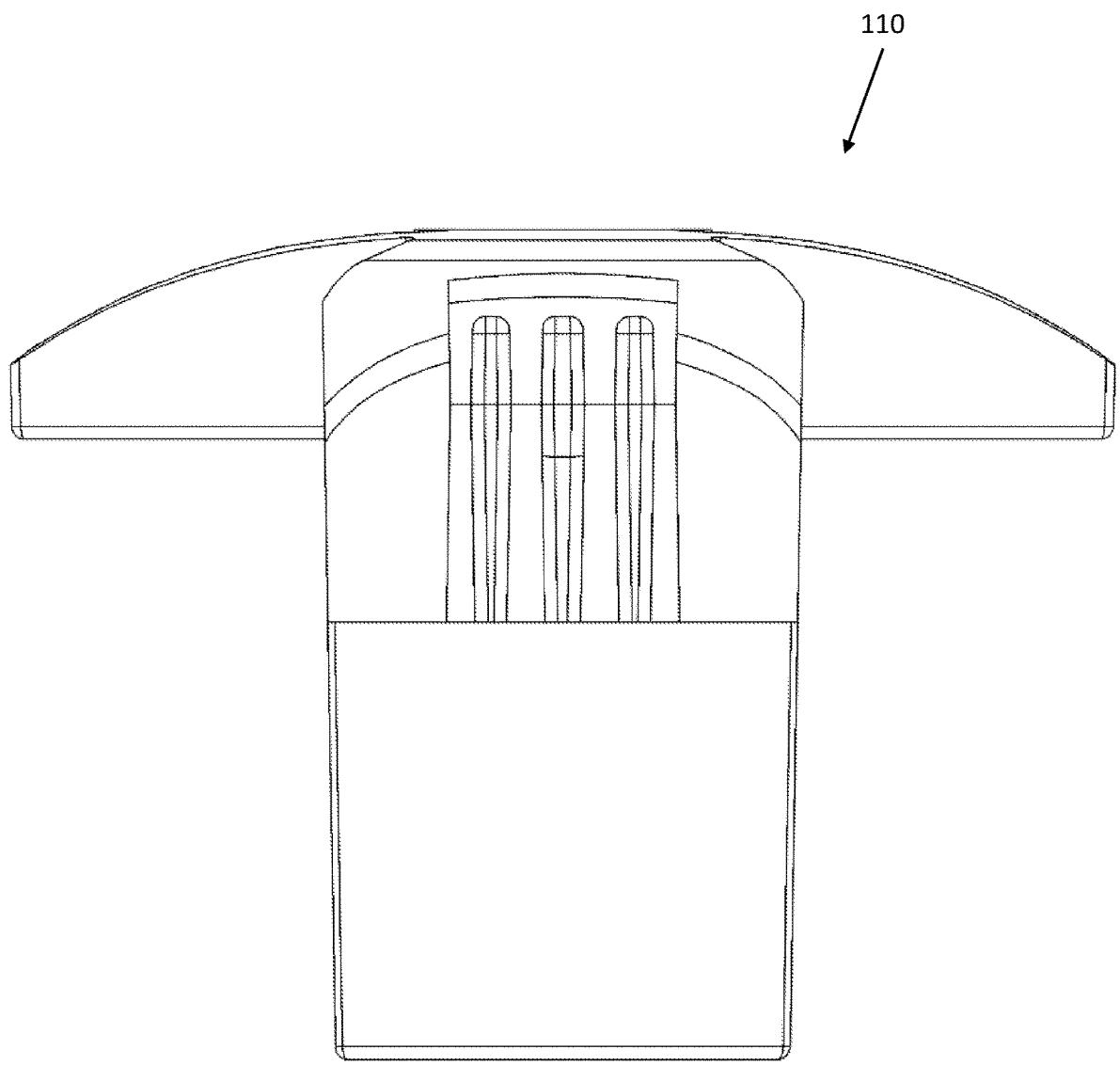
FIG. 22 is a back plan view of the circumcision device housing depicted in FIG. 1.
Figure 23:
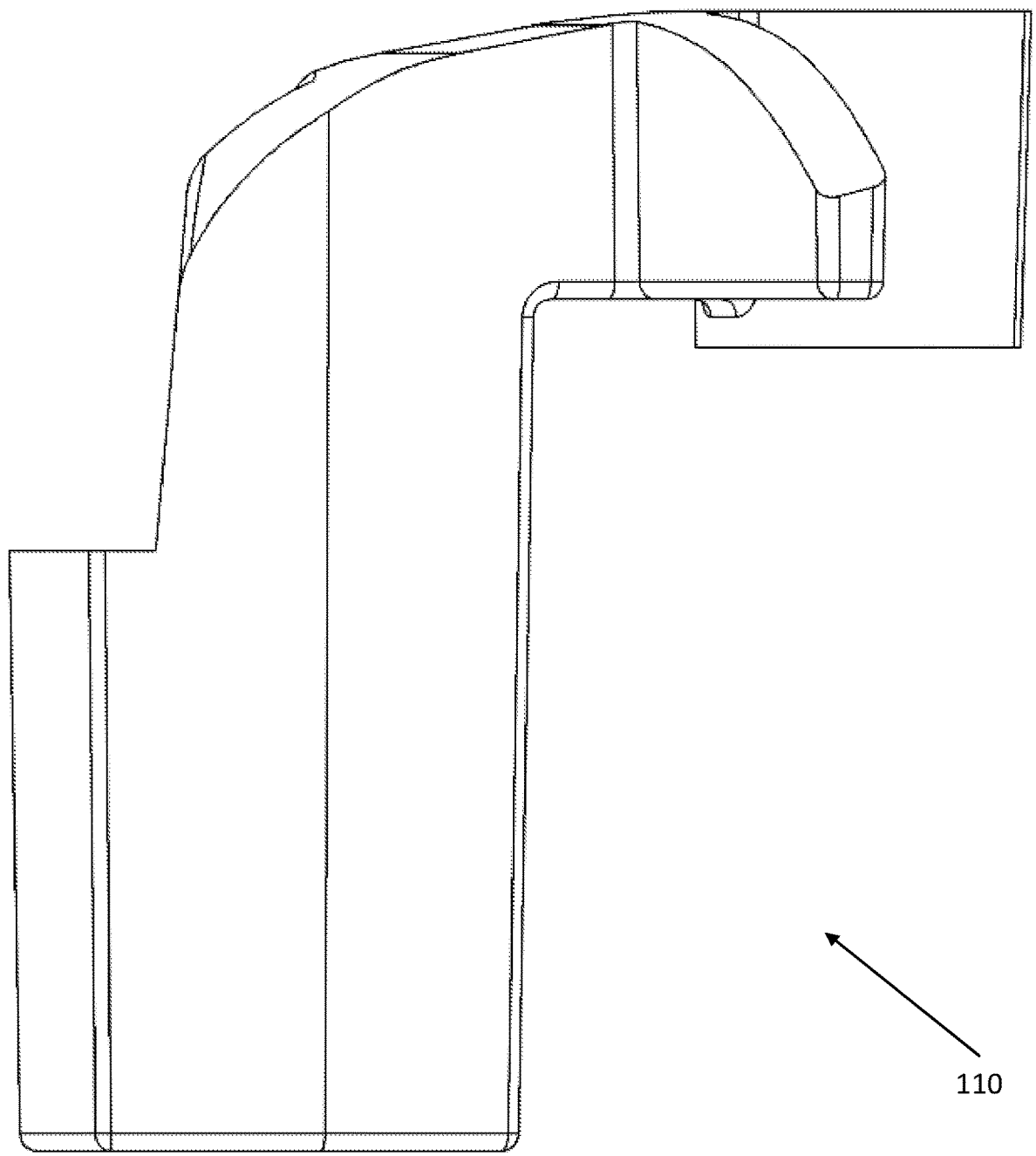
FIG. 23 is a left side elevational view of the circumcision device housing depicted in FIG. 1.
Figure 24:
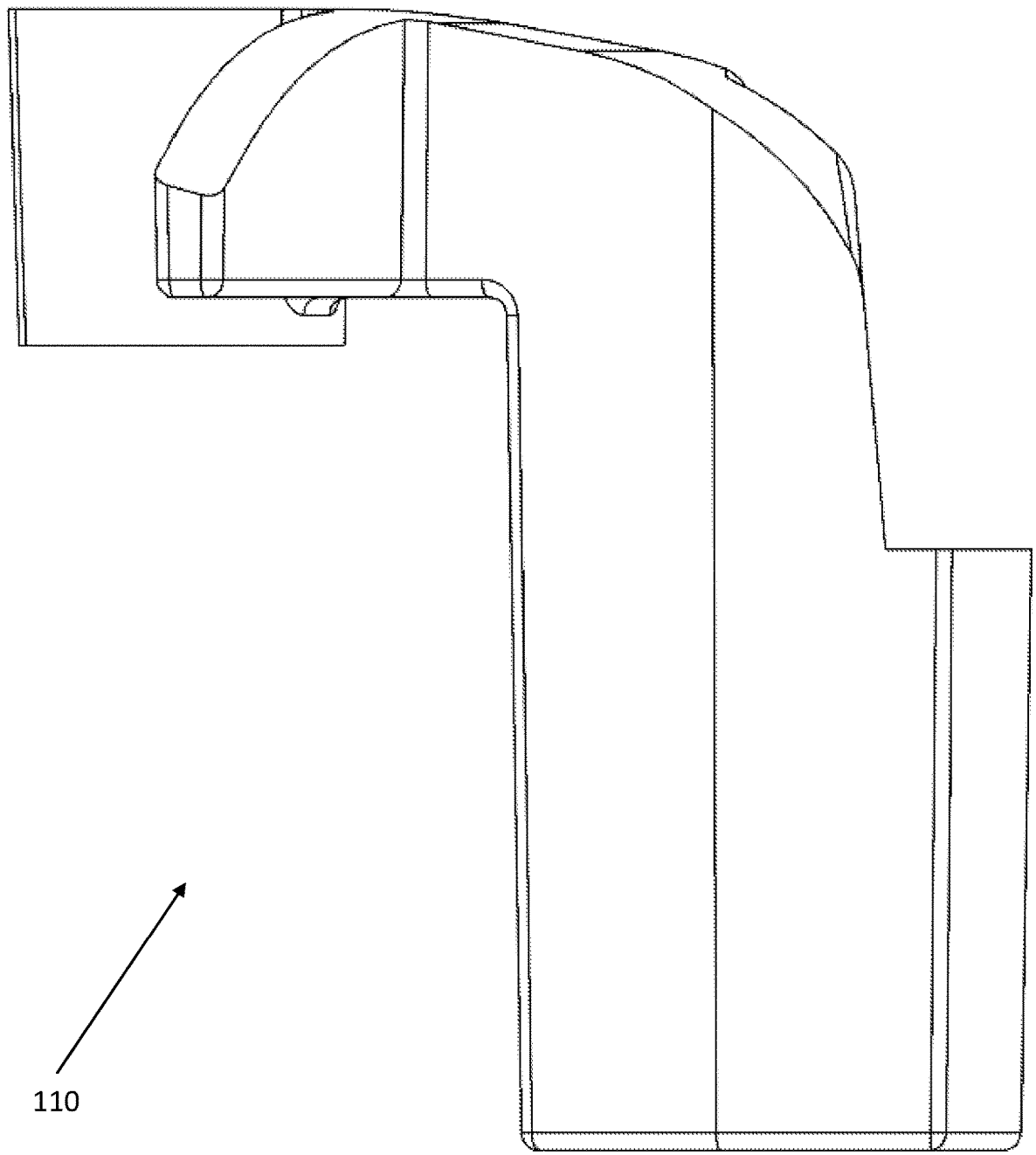
FIG. 24 is a right side elevational view of the circumcision device housing depicted in FIG. 1.
Figure 25:
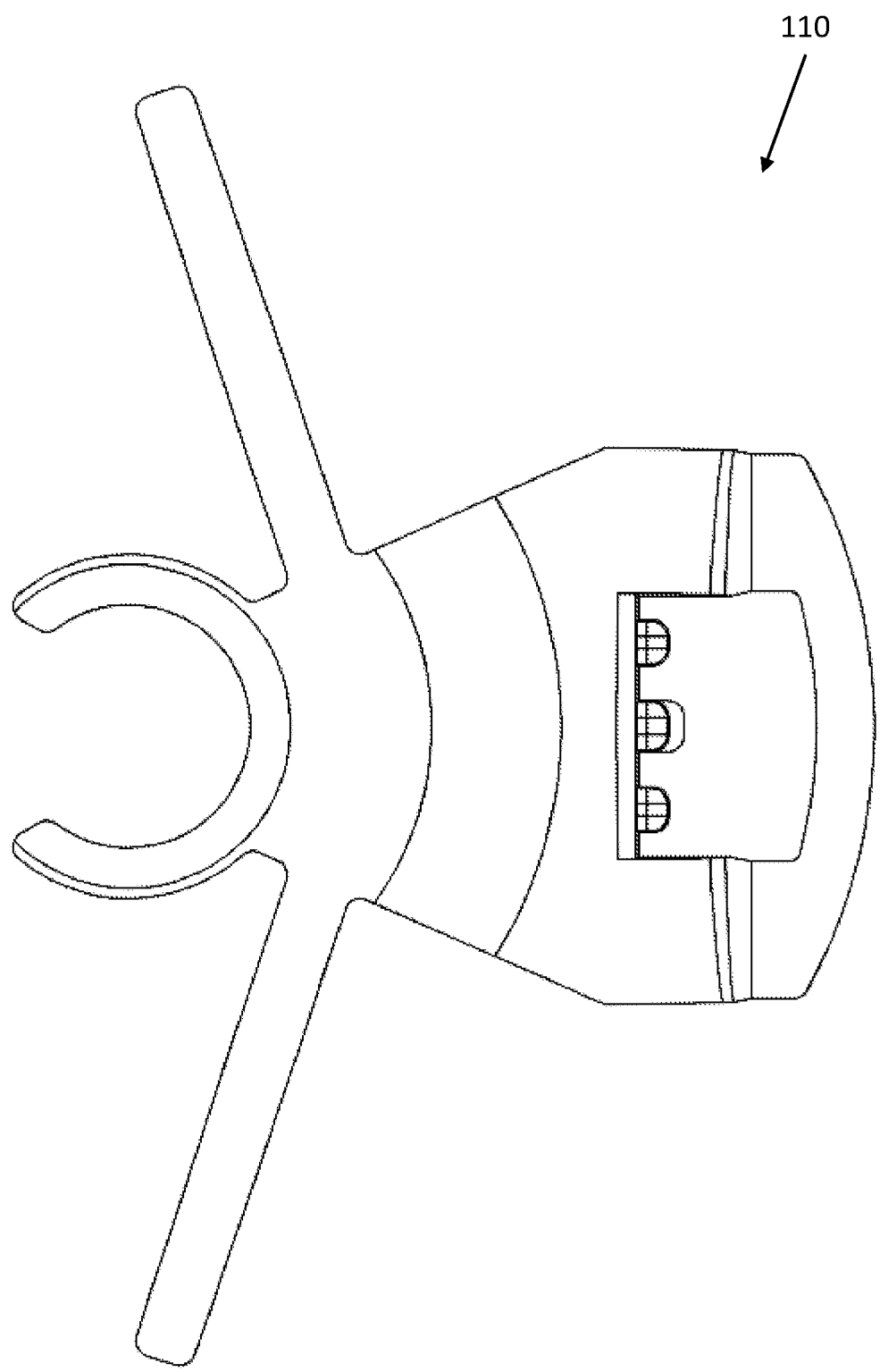
FIG. 25 is a top plan view of the circumcision device housing depicted in FIG. 1.
Figure 26:
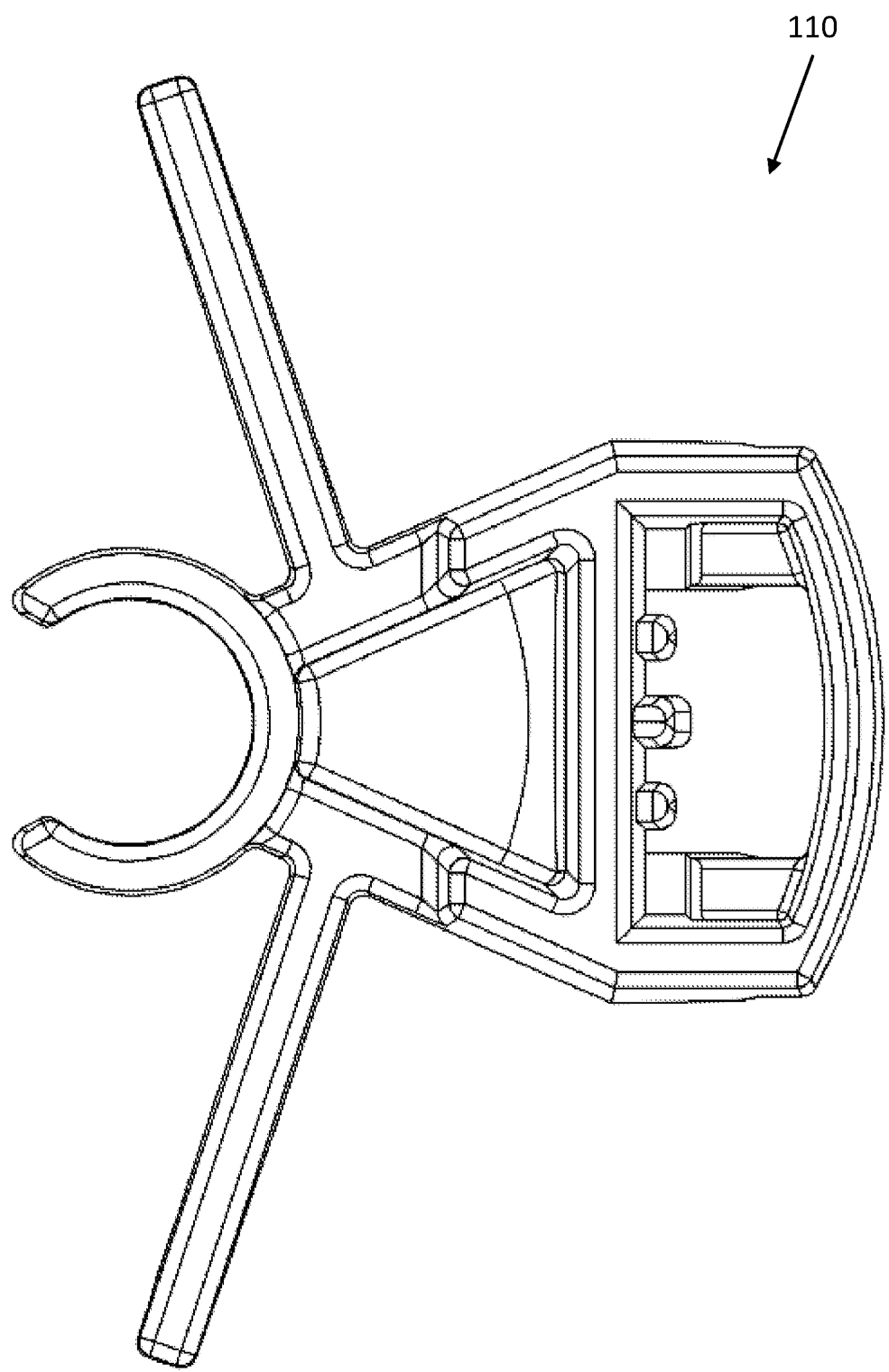
FIG. 26 is a bottom plan view of the circumcision device housing depicted in FIG. 1.
Figure 27:
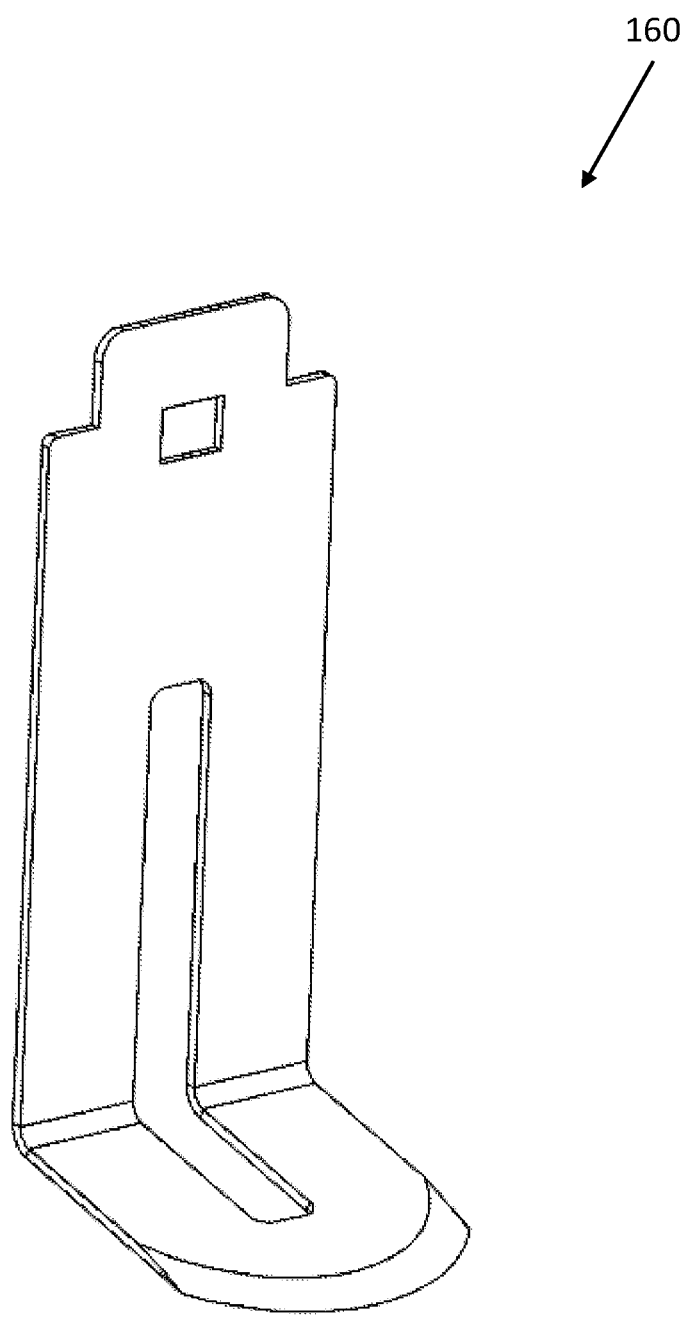
FIG. 27 is a perspective view of the front and right side of the cutting portion depicted in FIG. 4.
Figure 28:
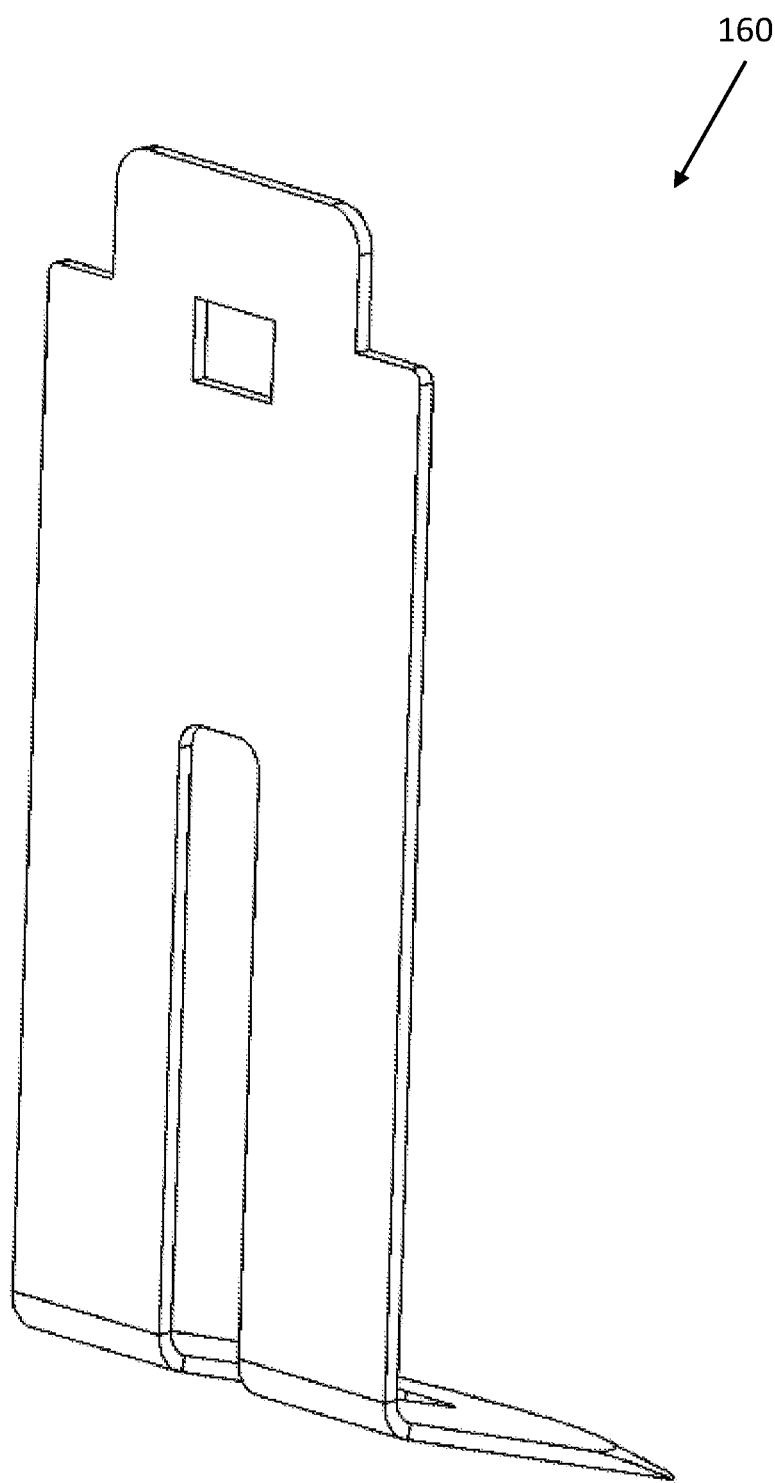
FIG. 28 is a perspective view of the back and right side of the cutting portion depicted in FIG. 4.
Figure 29:
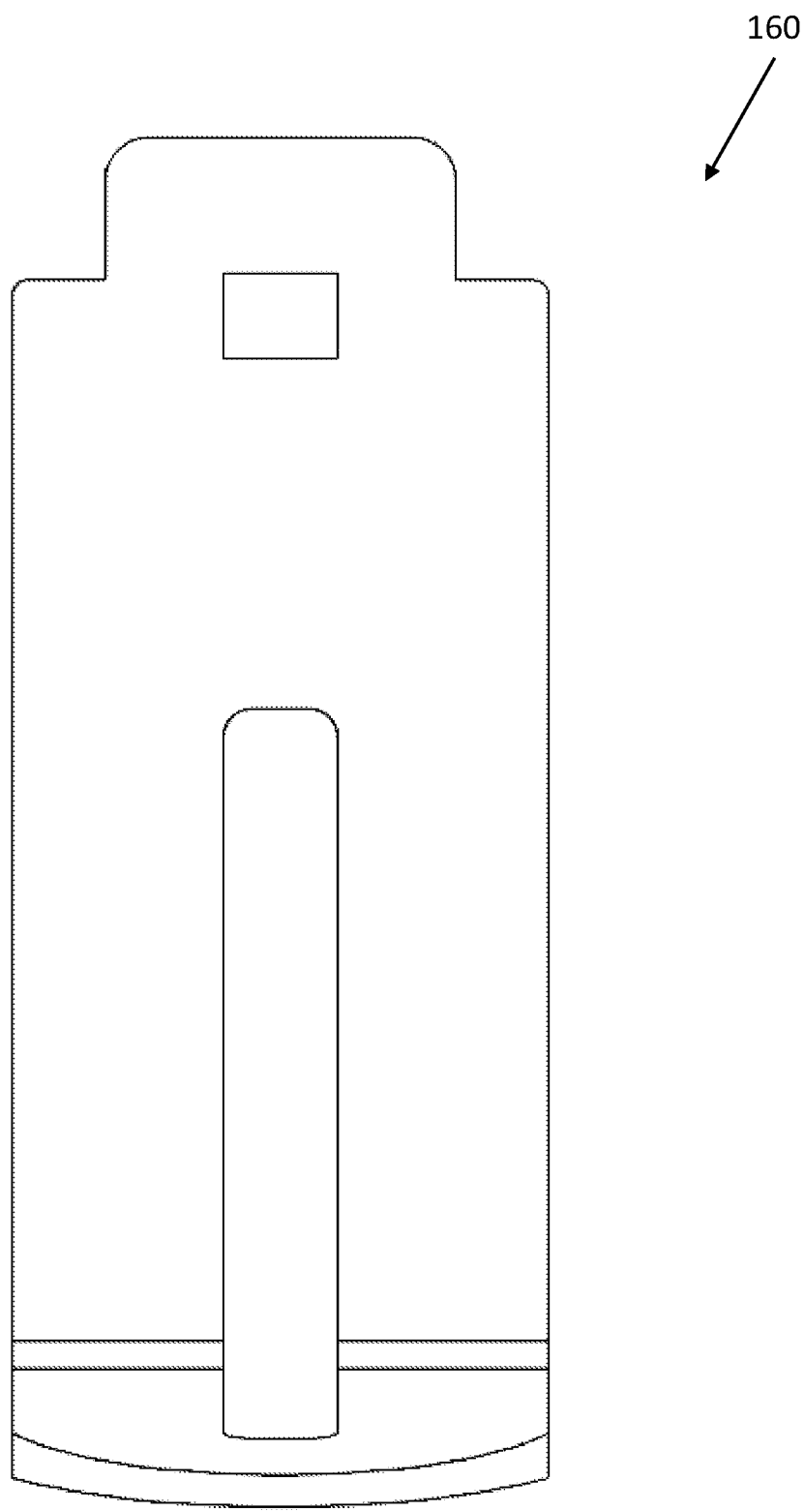
FIG. 29 is a front elevational view of the cutting portion depicted in FIG. 4.
Figure 30:
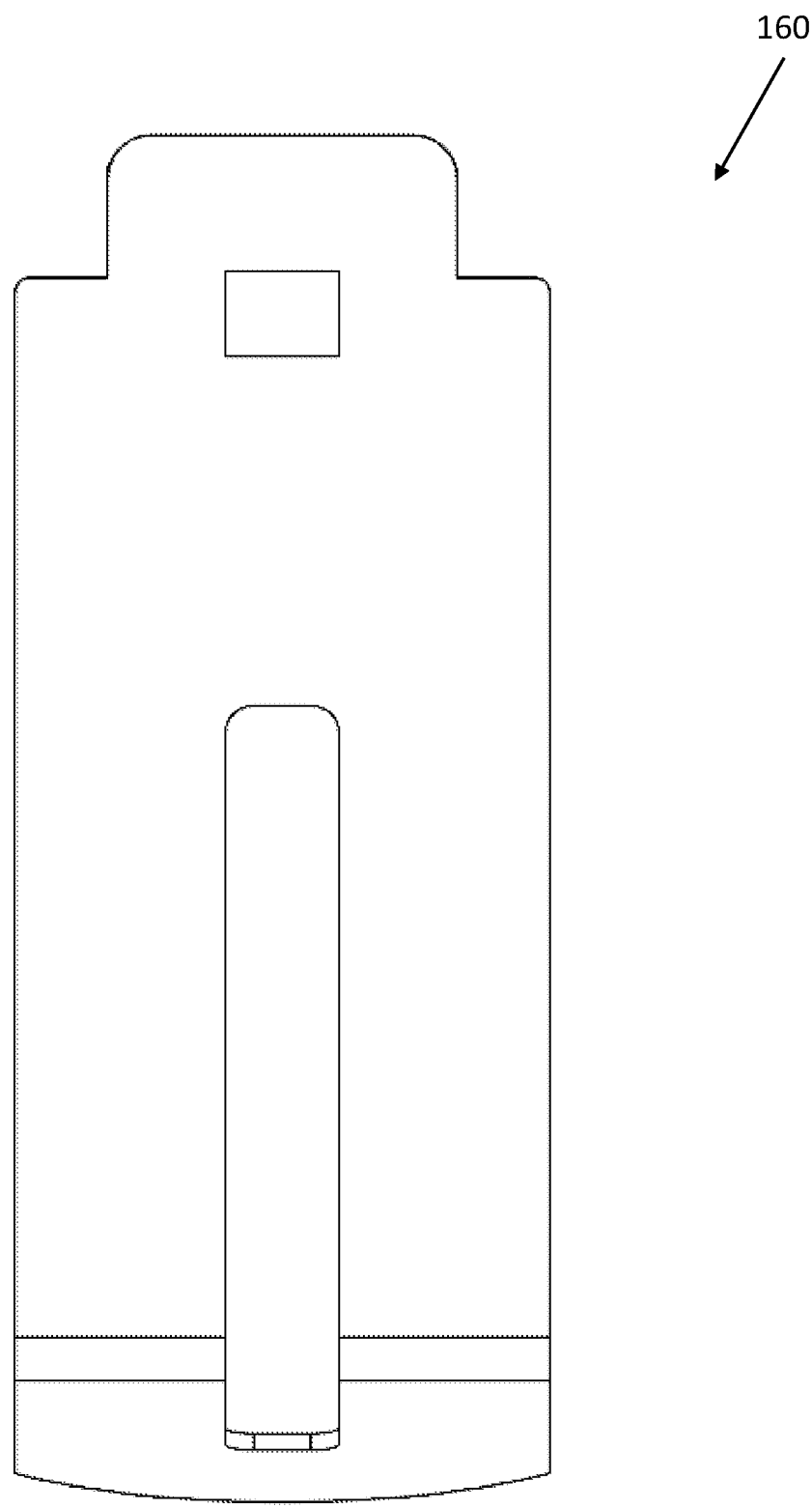
FIG. 30 is a back elevational view of the cutting portion depicted in FIG. 4.
Figure 31:
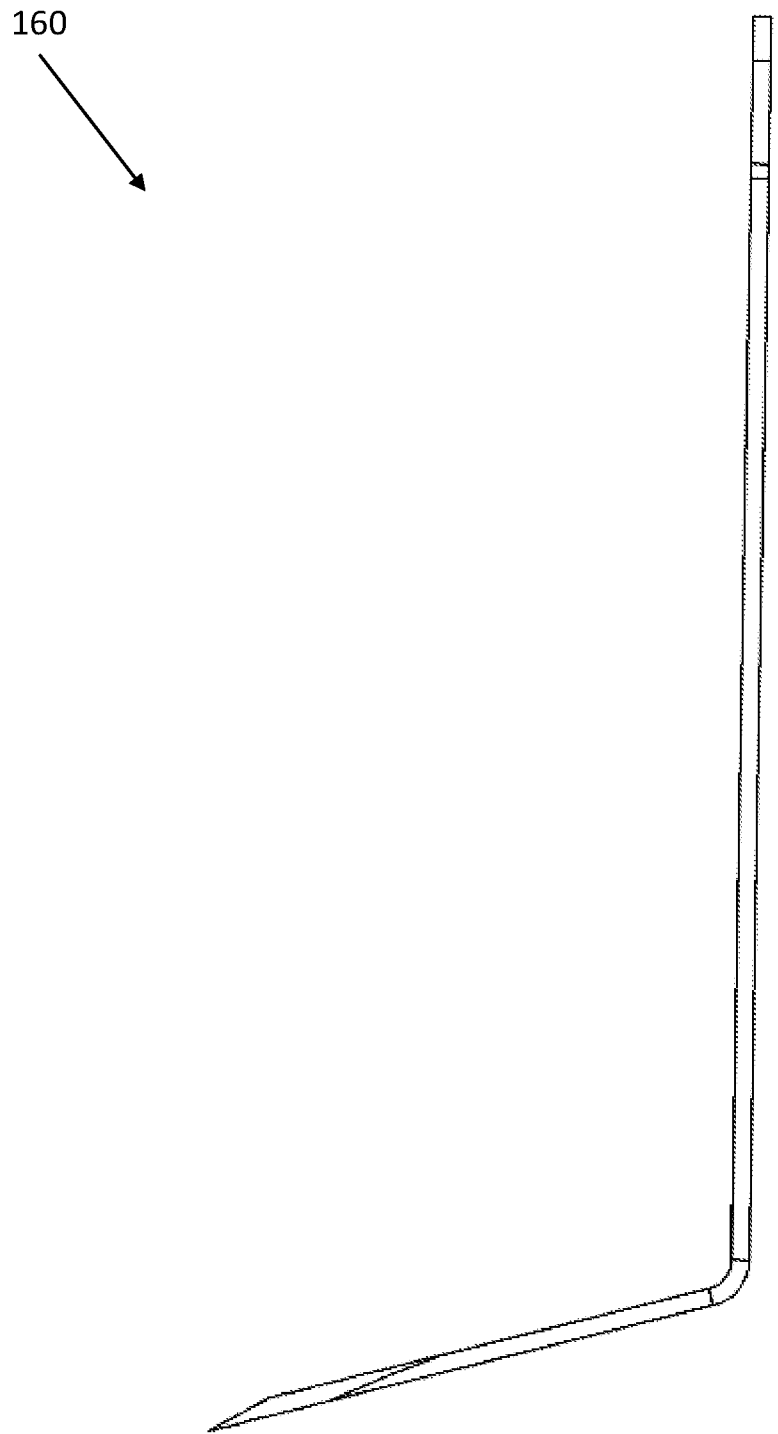
FIG. 31 is a left elevational view of the cutting portion depicted in FIG. 4.
Figure 32:
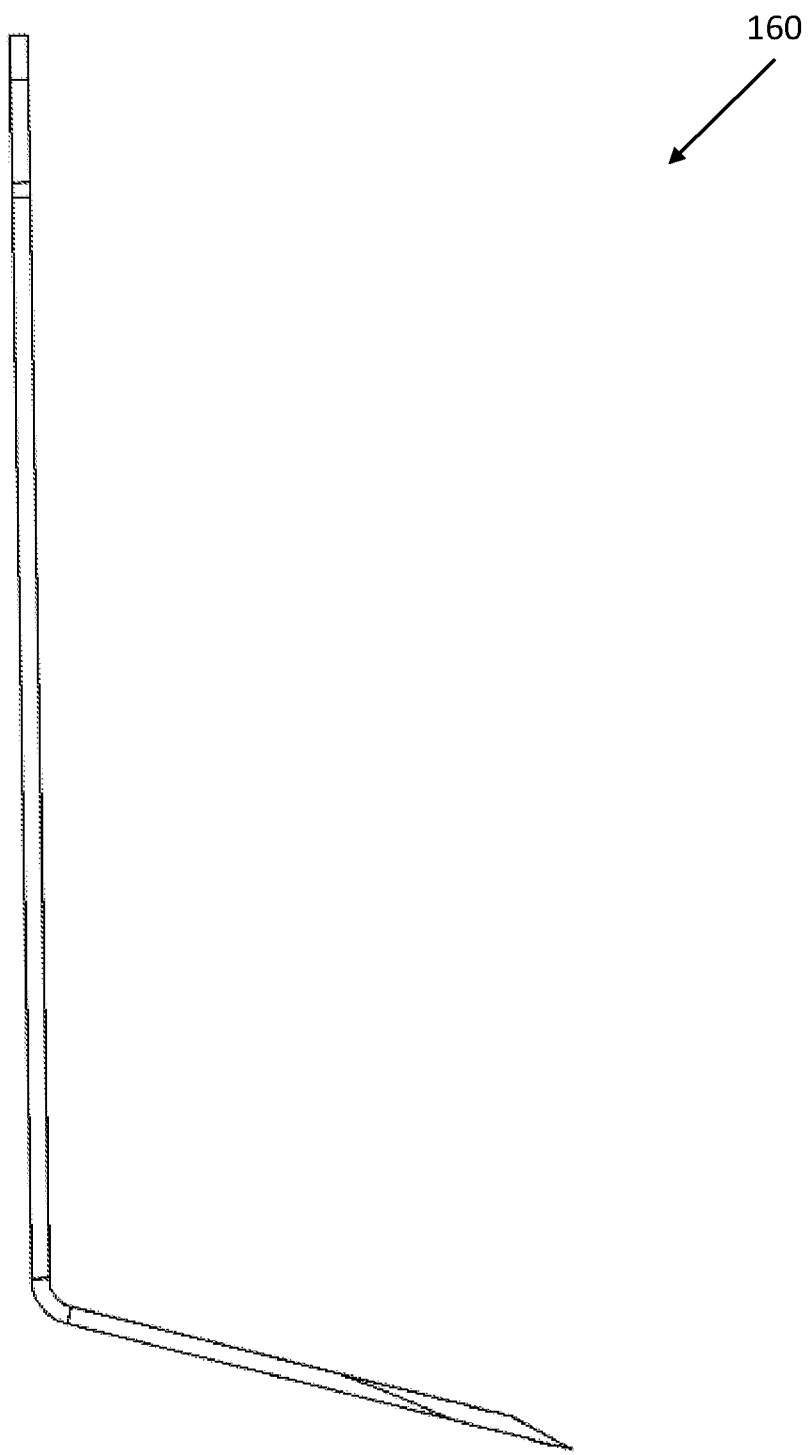
FIG. 32 is a right elevational view of the cutting portion depicted in FIG. 4.
Figure 33:
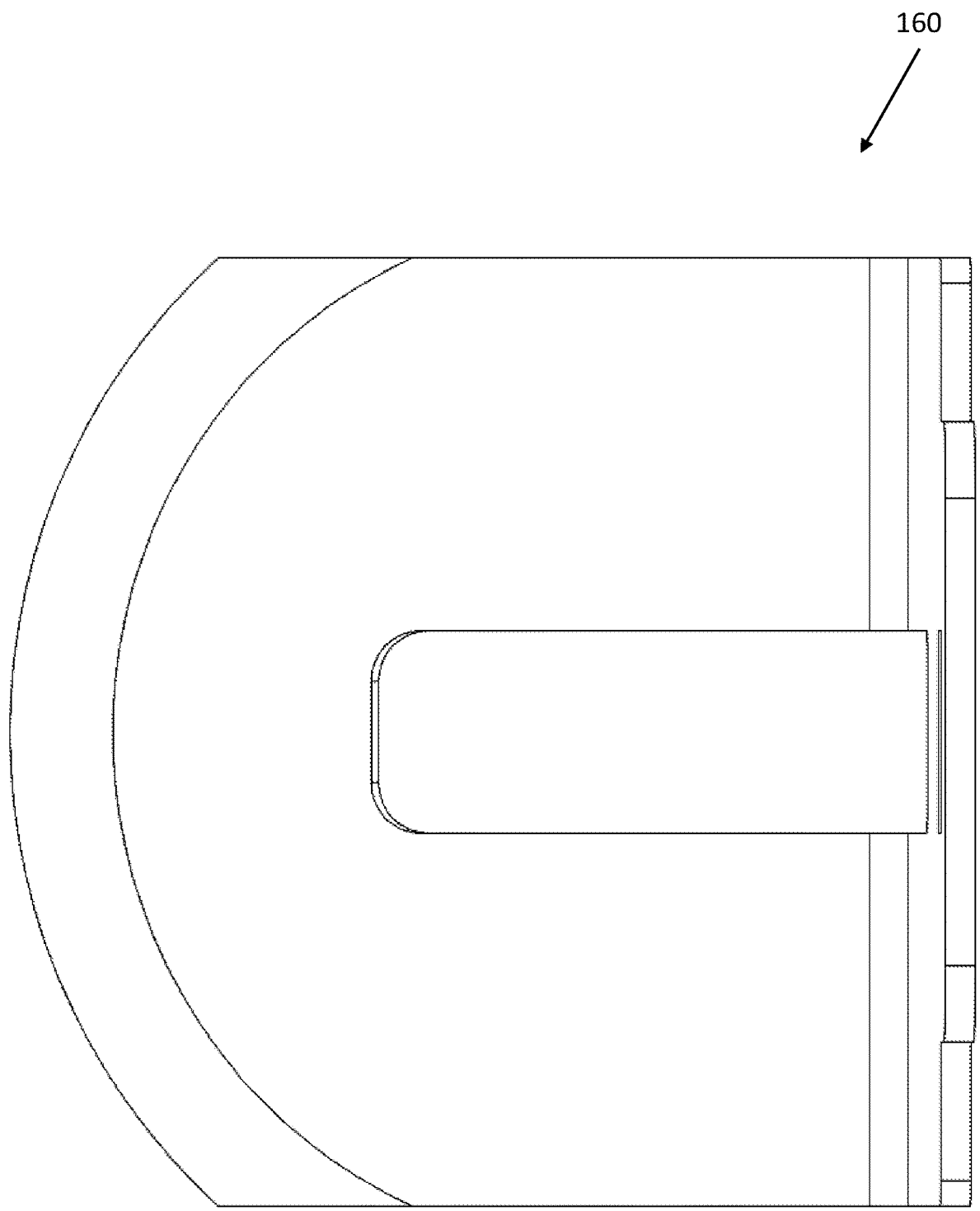
FIG. 33 is a top plan view of the cutting portion depicted in FIG. 4.
Figure 34:
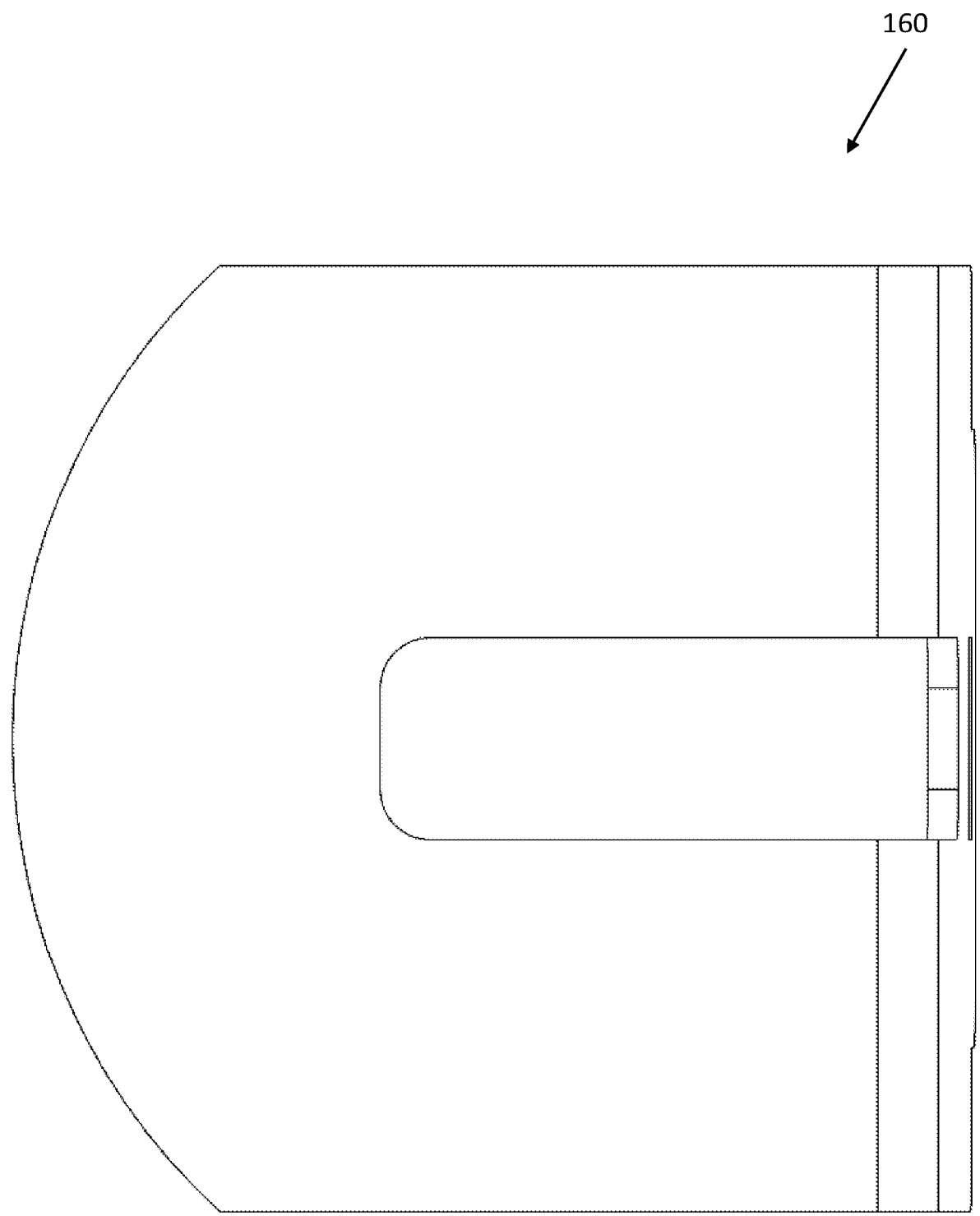
FIG. 34 is a bottom plan view of the cutting portion depicted in FIG. 4.

Referring to FIG. 10, safety features of embodiments of the present disclosure include the cutting device 160 being held in a position that is away from the patient's tissue if the circumcision device 100 is not properly connected to tissue holding member 190. For example, in some embodiments the distance 170 that the cutting edge 162 extends beyond the inner portion 131 of cutting device holder 130 is equal to or less than the distance 199 the outer edge 200 of the base plate 196 extends beyond the aperture 198 in base plate 196. This difference between distance 170 and distance 199 facilitates the cutting edge 162 of cutting device 160 being held a sufficient distance away from the patient's tissue to prevent the cutting edge 162 contacting the patient's tissue 900 when the circumcision device 100 is not properly connected to the tissue holding member 190. The angle at which the circumcision device is tilted away from alignment with the vertical extension 191 when circumcision device 100 in incorrectly attached to the tissue holding member 190 helps hold the cutting edge 162 away from the tissue 900, which can have enhanced benefits in embodiments where the distance 170 is approximately equal to, and potentially less than, the distance 199.

In some embodiments of the present disclosure, the housing 110 and the cutting device 160 are not two separate devices connected to one another, but are a single-piece (which may be referred to as being monolithic) integrated device.

Various aspects of different embodiments of the present disclosure are expressed in paragraphs X1, X2, and X3, as follows:

X1. One embodiment of the present disclosure includes a rotatable circumcision device, comprising: a connector configured and adapted to connect by hand to a tissue holding device while the tissue holding device is holding penile tissue, rotate around the tissue holding device when the connector is connected to the tissue holding device and the tissue holding device is holding penile tissue, and disconnect by hand from the tissue holding device while the tissue holding device is holding penile tissue; and a cutting device connected to the connector, wherein the cutting device is configured and adapted to cut the foreskin of the penile tissue being held by the tissue holding device when the connector is rotated around the tissue holding device.

X2. Another embodiment of the present disclosure includes a method for manufacturing a circumcision device, comprising: forming a connector including two distal ends, an inner surface defining a connector axis, and a first retaining member, wherein the two distal ends are capable of flexing without breaking while being pressed onto an elongated member defining an elongated member axis that is parallel to the connector axis when the connector is connected to the elongated member; and forming a cutting device with a cutting edge and a second retaining member configured and adapted to interact with the first retaining member and hold the cutting device and the connector together.

X3. Another embodiment of the present disclosure includes a rotatable circumcision device, comprising: a cutting device configured and adapted to cut the foreskin of a patient while being held by a tissue holding device; and means for hand connecting and hand disconnecting the cutting device from a tissue holding device while the tissue holding device is holding a patient's penile tissue.

Yet other embodiments include the features described in any of the previous statements X1, X2 or X3, as combined with
 (i) one or more of the previous statements X1, X2 or X3,
 (ii) one or more of the following aspects, or
 (iii) one or more of the previous statements X1, X2 or X3 and one or more of the following aspects:

Wherein the connector has two distal ends that separate then move closer together as the connector is hand connected to the tissue holding device.

Wherein the connector defines an axis.

One or more grip assist tabs extending perpendicularly to the axis, the one or more grip assist tabs configured and adapted to be manipulated by hand to rotate the connector around the axis when the connector is connected to a tissue holding device.

Wherein the one or more grip assist tabs are located at the same location along the axis as the connector.

Wherein the cutting device defines two planar surfaces.

Wherein the two planar surfaces are oriented at an oblique angle with respect to one another.

Wherein at least one of the two planar surfaces defines a slot.

Wherein the two planar surfaces define a slot extending between the two planar surfaces.

Wherein the oblique angle is at least 91 and at most 131 degrees.

Wherein the oblique angle is at least 100 and at most 110 degrees.

Wherein the cutting device defines a cutting edge configured and adapted to cut penile foreskin.

Wherein the tissue holding device to which the rotatable circumcision device connects defines a planar surface perpendicular to the axis when the connector is connected to the tissue holding device.

Wherein the cutting edge registers with the planar surface of the tissue holding device when the connector is connected to the tissue holding device.

Wherein the connector defines an elongated receptacle for receiving a planar surface of the cutting device.

Wherein the connector defines a retaining tab.

Wherein the retaining tab is located within the elongated receptacle.

Wherein the retaining tab defines a ramp that assists with securely connecting the cutting device to the connector.

Wherein pressure on the connector and in a direction perpendicular to the axis increases the pressure the cutting device exerts on the foreskin when the tissue holding device is connected to penile tissue.

Wherein the connector includes a cutting device holder.

Wherein the cutting device holder defines an inner portion that extends along the axis.

Wherein the inner portion of the cutting device inhibits the cutting device from contacting the patient's tissue when the patient's tissue is being held by the tissue holding device.

Wherein the tissue holding device resembles a Gomco clamp.

Connecting the connector and the cutting device together.

Connecting the connector and the cutting device together with the first retaining member and the second retaining member interacting with one another and holding the cutting device and the connector together Forming one or more arms extending in a direction perpendicular to the axis or the connector axis.

Wherein the one or more arms are configured and adapted to provide manipulation locations a user can use to rotate the connector around the connector axis when the connector is connected to an elongated member of a tissue holding member.

Wherein said forming one or more arms includes forming the one or more arms to be located at the same location along the connector axis as the connector.

Means for rotating the cutting device around a portion of the tissue holding device while the tissue holding device is holding a patient's penile tissue.

Means for pressing the cutting device onto a tissue holding device while the tissue holding device is holding a patient's penile tissue.

Wherein said means for rotating includes means for pressing the cutting device onto a tissue holding device while the tissue holding device is holding a patient's penile tissue.

Wherein said means for hand connecting and hand connecting includes a C-shaped member.

Wherein the connector includes a C-shaped portion.

Reference systems that may be used herein can refer generally to various directions (e.g., upper, lower, forward and rearward), which are merely offered to assist the reader in understanding the various embodiments of the disclosure and are not to be interpreted as limiting. Other reference systems may be used to describe various embodiments, such as referring to the direction of projectile movement as it exits the firearm as being up, down, rearward or any other direction.

To clarify the use of and to hereby provide notice to the public, the phrases "at least one of A, B, . . . and N" or "at least one of A, B, N, or combinations thereof" or "A, B, . . . and/or N" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. As one example, "A, B and/or C" indicates that all of the following are contemplated: "A alone," "B alone," "C alone," "A and B together," "A and C together," "B and C together," and "A, B and C together." If the order of the items matters, then the term "and/or" combines items that can be taken separately or together in any order. For example, "A, B and/or C" indicates that all of the following are contemplated: "A alone," "B alone," "C alone," "A and B together," "B and A together," "A and C together," "C and A together," "B and C together," "C and B together," "A, B and C together," "A, C and B together," "B, A and C together," "B, C and A together," "C, A and B together," and "C, B and A together."

While examples, one or more representative embodiments and specific forms of the disclosure have been illustrated and described in detail in the drawings and foregoing description, the same is to be considered as illustrative and not restrictive or limiting. The description of particular features in one embodiment does not imply that those particular features are necessarily limited to that one embodiment. Some or all of the features of one embodiment can be used or applied in combination with some or all of the features of other embodiments unless otherwise indicated. One or more exemplary embodiments have been shown and described, and all changes and modifications that come within the spirit of the disclosure are desired to be protected.

ELEMENT NUMBERING

Table 1 includes element numbers and at least one word used to describe the member and/or feature represented by the element number. It is understood that none of the embodiments disclosed herein are limited to these descriptions, other words may be used in the description or claims to describe a similar member and/or feature, and these element numbers can be described by other words that would be understood by a person of ordinary skill reading and reviewing this disclosure in its entirety.

TABLE 1

| | |
|---|---|
| 100 | circumcision device |
| 110 | housing |
| 112 | connector |
| 113 | distal end |
| 114 | grip assist tab |
| 115 | upper surface |
| 116 | axis |
| 130 | cutting device holder |
| 131 | inner portion |
| 132 | receptacle |
| 133 | outer surface |
| 134 | pressure member |
| 136 | cutting device retaining tab |
| 137 | upper surface |
| 138 | insertion direction |
| 139 | insertion stop |
| 140 | vertical direction |
| 141 | horizontal direction |
| 160 | cutting device |
| 162 | cutting edge |
| 163 | upper edge |
| 164 | slot |
| 166 | aperture |
| 167 | angle |
| 168 | insertion stop |
| 169 | height |
| 170 | distance |
| 171 | front surface |
| 173 | vertical portion |
| 174 | horizontal portion |
| 190 | tissue holding device |
| 191 | vertical extension |
| 192 | distance |
| 193 | bell |
| 194 | upper surface |
| 195 | lower surface |
| 196 | base plate |
| 197 | arm |
| 198 | aperture |
| 199 | distance |
| 200 | outer edge |
| 900 | tissue |
| 901 | glans |
| 902 | foreskin |

What is claimed is:

1. A rotatable circumcision device, comprising:
a connector defining a cylindrical surface separating two distal ends, wherein the two distal ends define a gap in the cylindrical surface and the two distal ends are biased to maintain the size of the gap, the connector configured and adapted to
connect by hand to a cylindrical member of a tissue holding device while the tissue holding device is holding penile tissue, wherein the distal ends initially separate enlarging the size of the gap then move closer together due to the biasing of the two distal ends as the connector is connected to the cylindrical member of the tissue holding device,
rotate around the tissue holding device when the connector is connected to the tissue holding device and the tissue holding device is holding penile tissue, and
disconnect by hand from the cylindrical member of the tissue holding device while the tissue holding device is holding penile tissue, wherein the distal ends initially separate enlarging the size of the gap then move closer together due to the biasing of the two distal ends as the connector is disconnected from the cylindrical member of the tissue holding device; and
a cutting device connected to the connector, wherein the cutting device is configured and adapted to cut the foreskin of the penile tissue being held by the tissue holding device when the connector is rotated around the tissue holding device.

2. The rotatable circumcision device of claim 1, wherein the cylindrical surface defines an axis, the rotatable circumcision device further comprising:
one or more grip assist tabs extending perpendicularly to the axis, the one or more grip assist tabs configured and adapted to be manipulated by hand to rotate the connector around the axis when the connector is connected to a tissue holding device.

3. The rotatable circumcision device of claim 2, wherein the one or more grip assist tabs are located at the same location along the axis as the connector.

4. The rotatable circumcision device of claim 1, wherein the cutting device includes two-planar sections oriented at an oblique angle with respect to one another.

5. The rotatable circumcision device of claim 4, wherein at least one of the two planar sections defines a slot.

6. The rotatable circumcision device of claim 4, wherein the oblique angle is at least 90 and at most 131 degrees.

7. The rotatable circumcision device of claim 4, wherein the cylindrical surface defines an axis,
the cutting device defines a cutting edge configured and adapted to cut penile foreskin,
the cutting edge is configured to register with a planar surface of the tissue holding device, wherein the planar surface is perpendicular to the axis when the connector is connected to the tissue holding device.

8. The rotatable circumcision device of claim 4, wherein the connector defines an elongated receptacle for receiving a planar surface of the cutting device and a retaining tab located within the elongated receptacle, wherein the retaining tab defines a ramp that assists with securely connecting the cutting device to the connector.

9. The rotatable circumcision device of claim 1, wherein the cylindrical surface defines an axis, and wherein pressure in a direction perpendicular to the axis and on the connector increases the pressure the cutting device exerts on the foreskin when the tissue holding device is connected to penile tissue.

10. The rotatable circumcision device of claim 1, wherein the cylindrical surface defines an axis,
the connector includes a cutting device holder that defines an inner portion that extends along the axis, and
the inner portion inhibits the cutting device from contacting the patient's tissue when the patient's tissue is being held by the tissue holding device.

11. The rotatable circumcision device of claim 1, wherein the tissue holding device to which the connector connects is a Gomco clamp.

12. A rotatable circumcision device for connecting to a tissue holding member and holding a tissue cutting device, comprising:
a housing defining a cutting device receptacle and a cylindrically shaped surface,
wherein the cutting device receptacle is configured and adapted to hold a tissue cutting device;
wherein the cylindrically shaped surface is configured and adapted to rotate around a cylindrical member of a tissue holding device while embracing the cylindrical member,
wherein the foreskin of a patient while being held by a tissue holding device is cut while the cutting device receptacle holds a tissue cutting device and the cylindrically shaped surface rotates around the cylindrical member of the tissue holding device; and means for snap-connecting and snap-disconnecting the cutting device from a tissue holding device while the tissue holding device is holding a patient's penile tissue.

13. The rotatable circumcision device of claim 12, further comprising:
means for rotating the cutting device around a portion of the tissue holding device while the tissue holding device is holding a patient's penile tissue.

14. The rotatable circumcision device of claim 13, wherein said means for rotating includes means for pressing the cutting device onto a tissue holding device while the tissue holding device is holding a patient's penile tissue.

15. The rotatable circumcision device of claim 12, wherein said means for hand connecting and hand disconnecting includes a C-shaped member.

16. The rotatable circumcision device of claim 12, wherein the cylindrically shaped surface defines an axis, the rotatable circumcision device further comprising:
one or more grip assist tabs extending perpendicularly to the axis, the one or more grip assist tabs located at the same location along the axis as the cylindrically shaped surface, the grip assist tabs being configured and adapted for hand manipulation to rotate the cylindrically shaped surface around the axis when the cylindrically shaped surface is embracing the cylindrical member.

17. The rotatable circumcision device of claim 12, wherein the tissue cutting device includes two planar sections oriented at an oblique angle with respect to one another, wherein the oblique angle is at least 90 and at most 131 degrees.

18. The rotatable circumcision device of claim 17, wherein
at least one of the two planar sections of the tissue cutting device defines a slot,
the housing defines an elongated receptacle and a retaining tab located within the elongated receptacle,
the elongated receptacle being configured and adapted to receive a planar section of the tissue cutting device and
the retaining tab defining a ramp that assists with securely connecting the tissue cutting device to the housing.

19. The rotatable circumcision device of claim 12, wherein
the tissue holding device to which the cylindrically shaped surface connects is a Gomco clamp, the cylindrical member of the Gomco clamp defines an axis, and the Gomco clamp includes a planar surface perpendicularly oriented to the cylindrical member,
the tissue cutting device defines a cutting edge configured and adapted to cut penile foreskin, and
the cutting edge is configured to register with the planar surface of the Gomco clamp when the cylindrically shaped surface is embracing the cylindrical member of the Gomco clamp.

20. The rotatable circumcision device of claim 12, wherein
the cylindrically shaped surface defines an axis,
the housing includes an inner portion adjacent the cutting device receptacle and extending along the axis, and
the inner portion inhibits a tissue cutting device from contacting the patient's tissue when the cutting device receptacle holds the tissue cutting device and the patient's tissue is held by the tissue holding device.

* * * * *